United States Patent [19]
Labrie et al.

[11] Patent Number: 6,015,806
[45] Date of Patent: Jan. 18, 2000

[54] ANTIANDROGENS

[75] Inventors: Fernand Labrie; Yves Merand; Shankar M. Singh, all of Ste-Foy, Canada

[73] Assignee: Endorecherche, Quebec, Canada

[21] Appl. No.: 08/478,973

[22] Filed: Jun. 7, 1995

Related U.S. Application Data

[60] Division of application No. 08/060,612, May 17, 1993, which is a continuation-in-part of application No. 08/196,332, Feb. 14, 1994, Pat. No. 5,494,914, which is a division of application No. 07/886,961, May 21, 1992, abandoned.

[51] Int. Cl.$^7$ .................................................. A61K 31/56
[52] U.S. Cl. ............................................................ 514/178
[58] Field of Search ............................................... 514/178

[56] References Cited

U.S. PATENT DOCUMENTS

| | | | |
|---|---|---|---|
| 4,039,669 | 8/1977 | Beylen et al. | 424/243 |
| 5,132,106 | 7/1992 | Tuloup et al. | 424/70 |
| 5,364,847 | 11/1994 | Labrie et al. | 514/182 |

FOREIGN PATENT DOCUMENTS

| | | |
|---|---|---|
| 10669/88 | 7/1988 | Australia . |
| 10778/88 | 8/1988 | Australia . |
| 31569/89 | 9/1989 | Australia . |
| 1917087 | 11/1969 | Germany . |
| 1199993 | 11/1989 | Japan . |
| 1081494 | 8/1967 | United Kingdom . |
| 2025422 | 1/1980 | United Kingdom . |
| 8502543 | 6/1985 | WIPO . |
| 9100732 | 1/1991 | WIPO . |

OTHER PUBLICATIONS

Weikel, et al., *Journal of Toxicology & Environ. Health*, 3:167–177 (1977).
Thornber, *Chemical Society Reviews* 8(4): 563–580 (1979).
Salman, et al., *J. Steroid Biochem* 33(1):25–31 (1989).
Patent Abstracts of Japan, 4(38), JP Appln. 790077047, (1980).
Declaration from file wrapper of Republic of China (Taiwan) application 9106669 published Apr. 11, 1992 and English basis.

*Primary Examiner*—Jose' G. Dees
*Assistant Examiner*—Alton Pryor
*Attorney, Agent, or Firm*—Ostrolenk, Faber, Gerb & Soffen, LLP

[57] ABSTRACT

Androgen nucleus derivatives having specified substituents at the 17α position are disclosed for use as antiandrogens for the treatment of androgen-dependent diseases. In some preferred embodiments, the compound

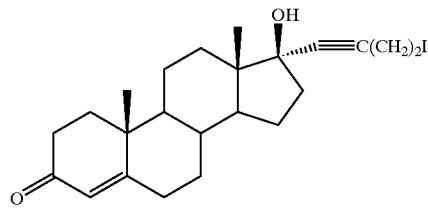

EM-250 is formulated together with pharmaceutically acceptable diluent or carrier for topical use in the treatment of androgen-dependent diseases associated with the skin.

7 Claims, No Drawings

ANTIANDROGENS

RELATED APPLICATIONS

This is a division of application Ser. No. 08/060,612, filed May 17, 1993; and is also a continuation-in-part of U.S. application Ser. No. 08/196,332, filed Feb. 14, 1994 (now U.S. Pat. No. 5,494,914), which is in turn a division of U.S. application Ser. No. 07/886,961, filed May 21, 1992 (now abandoned).

BACKGROUND OF THE INVENTION

This invention relates to novel inhibitors of sex steroid activity such as antiandrogen compounds having effective antagonistic activity while substantially lacking agonistic effects. More particularly, certain preferred embodiments of the invention relate to certain testosterone analogs which have high affinity for androgen receptors but do not activate such receptors. Some antiandrogens may additionally inhibit the production of sex steroids or their precursors.

BRIEF DESCRIPTION OF THE PRIOR ART

During the treatment of certain androgen dependent diseases, it is important to greatly reduce or, if possible, to eliminate androgen-induced effects. For this purpose, it is desirable to both block access to the androgen receptors with "antiandrogens", thus preventing androgens from binding and activating those receptors, and also to reduce the concentration of androgens available to activate the receptors. It is possible that, even in the absence of androgens, unoccupied androgen receptors may be biologically active. Hence, antiandrogens which bind and block the receptors may produce better therapeutic results than therapy which only inhibits androgen production.

Antiandrogens may have a significant therapeutic effect in slowing or stopping the progress of androgen-dependent diseases, e.g. diseases whose onset or progress is aided by androgen receptor activation.

It is desired that an antiandrogen used in therapy to reduce androgen receptor activation have both good affinity for the androgen receptor and a substantial lack of inherent androgenic activity. The former refers to the ability of an antiandrogen to bind to the androgen receptor, and thus to block access to the receptor by androgens. The latter refers to the effect the antiandrogen has on the receptor once it binds thereto. Some antiandrogens may possess inherent androgenic activity ("agonistic activity") which undesirably activates the very androgen receptors whose activation they are intended to prevent. In other words, an antiandrogen with intrensic androgenic activity may successfully bind to androgen receptors, desirably blocking access to those receptors by natural androgens, yet may undesirably itself activate the receptor.

Known non-steroidal antiandrogens such as flutamide and anandron lack undesirable androgenic activity, but may not have receptor affinity as good as steroidal antiandrogens (i.e. androgen derivatives having a steroidal nucleus that is modified to provide antiandrogenic activity). Steroidal antiandrogens, however, are believed more likely to possess undesirable agonistic characteristics.

In the parent application hereto, the international counterpart of which was published on Jan. 24, 1991 as international publication number WO 91/00732. Applicants disclosed novel steroidal antiandrogens including compounds with a steroidal nucleus having novel substitutions at the 17α-position. The published parent application included 17α-haloalkynyl substituents. Examples of numerous 17α-iodoalkynyl substituents ranging in size from iodopentynyl to iodododecynyl are set forth in the examples. As discussed in detail infra, it has now been discovered that overall effectiveness of antiandrogenic compounds is greatly enhanced by carefully controlling the size, configuration and identity of the 17α-substituent and especially by limiting it as described and claimed herein.

Certain nortestosterone compounds having certain 17α-haloalkynyl sidechains were used for different and non-pharmaceutical purposes by Salmon et al. ((1); J Steroid Biochem Vol 33, No 1, pp 25–31 (1989); and (2); J. Steroid Biochem Vol 26, No 3, pp 383–91 (1987)).

International publication WO 92/05763 describes certain 16,16-disubstituted androstene compounds for treatment of androgen dependent skin disorders.

European patent publication 0 435 321 describes certain 17-substituted A-norsteroid-3-carboxylic acid derivatives for use in the inhibition of mammalian 5α-reductase activity.

SUMMARY OF THE INVENTION

It is an object of the present invention to provide improved antiandrogens, having good affinity for the androgen receptor, while substantially lacking androgenic activity. These antiandrogens may be useful in the treatment of androgen-dependent diseases as described in more detail infra.

In one aspect, the invention provides an antiandrogenic compound of the molecular formula:

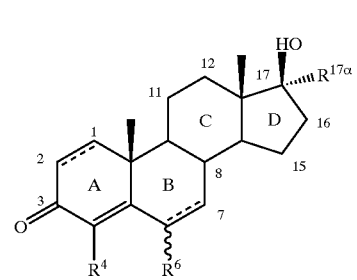

I

Wherein the dotted lines are optional pi bonds;
Wherein $R^4$ is —H or —CH$_3$;
Wherein $R^6$ is —H, —CH$_3$, —CH$_2$CH$_3$ or halogen;
and wherein $R^{17\alpha}$ is selected from the group consisting of:
A) an unsaturated hydrocarbon moiety having at least one carbon atom that is separated from the D-ring of molecular formula I by at least three intervening atoms and having no carbon atom that is separated from said D-ring by more than four intervening atoms,
B) a halogenated unsaturated hydrocarbon moiety having at least one halogen atom that is separated from said D-ring by at least 3 intervening atoms, and having no carbon atom separated from said D-ring by more than four intervening atoms and
C) a haloalkyl moiety having at least one halogen atom separated from said D-ring by at least three intervening atoms and having no carbon atom separated from said D-ring by more than 4 intervening atoms.

In another aspect the invention provides a prodrug which is converted in vivo to the foregoing.

In another aspect the invention provides an an antiandrogenic compound of the molecular formula:

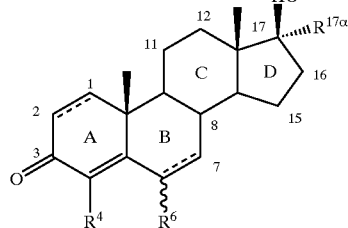

Wherein the dotted lines are optional pi bonds;
Wherein $R^4$ is —H or —$CH_3$;
Wherein $R^6$ is —H, —$CH_3$, —$CH_2CH_3$ or halogen;
and wherein $R^{17\alpha}$ is selected from the group consisting of:
A) an unsaturated hydrocarbon moiety having at least one carbon atom that is separated from the D-ring of molecular formula I by at least three intervening atoms and having no carbon atom that is separated from said D-ring by more than four intervening atoms,
B) a halogenated unsaturated hydrocarbon moiety having at least one halogen atom that is separated from said D-ring by at least 3 intervening atoms, and having no carbon atom separated from said D-ring by more than four intervening atoms and
C) a haloalkyl moiety having at least one halogen atom separated from said D-ring by at least three intervening atoms and having no carbon atom separated from said C-ring by more than 4 intervening atoms.
provided that $R^{17\alpha}$ is not

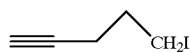

When $R^4$ and $R^6$ are both hydrogen. In another aspect, $R^{17\alpha}$ is not

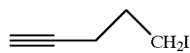

regardless of the identity of $R^4$ and $R^6$.

In another aspect, the invention provides topical or systemic pharmaceutical compositions containing the antiandrogens of the invention together with pharmaceutically acceptable diluents or carriers.

In another aspect, the novel antiandrogens, or pharmaceutical compositions containing them, are used in the treatment or prevention of androgen-dependent skin related diseases such as acne, hirsutism, seborrhea, androgenic alopecia, premature male baldness and the like.

In another aspect, they are used in the treatment or prevention of androgen-dependent systemic diseases such as prostate cancer or benign prostatic hyperplasia.

Except where otherwise specified, substituents to the steroidal nucleus of the antiandrogens of the invention may have α or β stereochemistry. Optional pi bonds denoted by dotted lines in a molecular structure are independent of any other optional bonds appearing in that structure, the presence of one not being dependent on the presence or absence of another, unless valence requires interdependency. Compounds discussed herein may be formulated as prodrugs which are converted in vivo to the desired active compound.

Atoms of the steroidal nucleus for which no substituent is shown may optionally be further substituted (as valence permits) so long as such substitution does not substantially and adversely affect the compound's affinity for the androgen receptor, and does not render the compound substantially more androgenic.

As used herein, the term "lower" when describing a chemical moiety means a moiety having 8 or fewer atoms. For instance, a "lower alkyl" means a $C_1$ to $C_8$ alkyl. Any moiety of more than two atoms may be straight- or branch-chained unless otherwise specified.

DETAILED DESCRIPTION OF THE PREFERRED EMBODIMENTS

The antiandrogens and pharmaceutical compositions containing them, may be utilized in accordance with the invention in the treatment of androgen-dependent diseases whose progress is aided by activation of androgen receptors, e.g. prostrate cancer, benign prostatic hyperplasia, acne, seborrhea, hirsutism, androgenic alopecia, premature male baldness and the like.

The 17α-substituent, of the antiandrogens of the invention may be either branched or straight-chain. It is preferred that the longest chain have from 4–5 carbon atoms straight-chain species are preferred. Unsaturated species are also preferred, as are halogenated species. It is preferred that unsaturated species be unsaturated at least at a position α, β to the steroids D-ring. Iodo-substituted 17α-species (e.g. EM 250 discussed below) are also preferred.

Halogenated species may be halogenated in more than one location. Likewise, unsaturated species may be unsaturated at multiple locations, e.g.

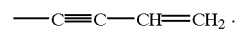

It is preferred that the optional double bond at the 4 position of the steroid A-ring be present. Preferred $R^{17\alpha}$ substituents include but are not limited to butynyl, butenyl, pentynyl, pentenyl, halobutynyl, halobutenyl, halopentynyl, halopentenyl, halobutyl and halopentyl. Other preferred species include but are not limited to $CH_2CH_2CH$=$CHX$ and

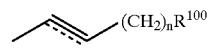

wherein $R^{100}$ is selected from the group consisting of H, F, Cl, Br and I, and wherein n is 2 or 3, and wherein the dotted line is an optional pi bond. Halobutynyl and halobutenyl are especially preferred.

EM-250 is an especially preferred antiandrogen for topical use because it is believed to have no antiandrogenic effect systemically, notwithstanding its substantial antiandrogenic effect when used topically. Thus any inadverment transdermal penetration which might occur during topical use of EM-250 is not expected to cause undesirable systemic effects.

In another aspect the invention provides a prodrug which is converted in vivo to

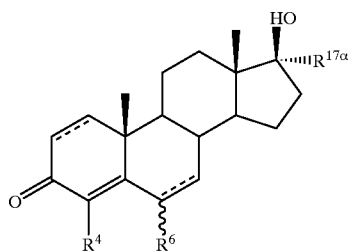

Wherein the dotted lines are optional pi bonds;
Wherein $R^4$ is —H or —$CH_3$;
Wherein $R^6$ is —H, —$CH_3$, —$CH_2CH_3$ or halogen; and
Wherein $R^{17\alpha}$ is selected from the group consisting of:
A) an unsaturated hydrocarbon moiety having at least one carbon atom that is separated from the D-ring of molecular formula I by at least three intervening atoms and having no carbon atom that is separated from said D-ring by more than four intervening atoms,
B) a halogenated unsaturated hydrocarbon moiety having at least one halogen atom that is separated from said D-ring by at least 3 intervening atoms, and having no carbon atom separated from said D-ring by more than four intervening atoms and
C) a haloalkyl moiety having at least one halogen atom separated from said D-ring by at least three intervening atoms and having no carbon atom separated from said D-ring by more than 4 intervening atoms.

There are many known modifications to chemical moieties such as the —OH or keto groups of an active compound which result in prodrug forms of the compound, said prodrug forms being convertable in vivo to the active compound, e.g. by hydrolysis, enzyme catalysis, or the like. Preferred prodrug forms in accordance with the invention have a substitution at the 3 position of the steroidal nucleus which converts in vivo to 3-keto. Among the preferred 3-substituents of the preferred prodrug forms are selected from the group of substituted or non substituted moieties consisting of:

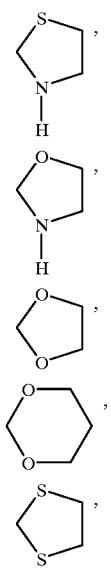

As explained in more detail infra, placing certain of these substituents at the 3-position can cause the steroidal double bonds to shift, resulting in a preferred prodrug of the formula:

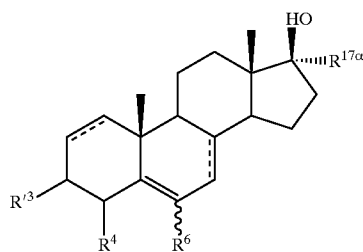

During use, the 3-position is converted back to =O and the double bond shift also reverses, resulting in the preferred active antiandrogens.

Some non-limiting examples of preferred active compounds, and of preferred prodrug modifications thereof, are discussed below together with preferred synthesis techniques.

EXAMPLE 1

Synthesis of 17α-(4'-chlorobutynyl)-17β-hydroxy-4androsten-3-one (EM 248)

Synthesis Described in Scheme 1

Thioketal 2

To a solution of testosterone 1 (288.43 g, 1.0 mole) (available from Schering A.G. germany) in glacial acetic acid (2.5 l), ethanedithiol (85 ml, 1.06 mole) and boron trifluoride etherate (800 ml) were added at 10° C. The mixture was stirred at this temperature for 1 h and poured over ice (2 kg). From the aqueous phase, a white solid was separated, collected by filtration, washed with water (2×2 L) and air dried. Crystallization from methanol gave the pure Thioketal 2. Yield: 328.28 g (90%). $^1$H NMR δ ($CDCl_3$, 300 MHz, TMS): 0.74 (s, 3H, 18$CH_3$), 1.03 (s, 3H, 19$CH_3$), 3.14–3.42 (m, 4H, S$CH_2$), 3.60 (t, 1H, J 8.4 Hz, 17αH), 5.47 (s, 1H, C-4H).

Ketone 3

Method A

A solution of Thioketal 2 (182.3 g, 0.5 mole) in dry dichloromethane (1.5 L) was added dropwise to a solution of pyridinium chlorochromate (150 g, 0.7 mole), molecular sieves 3A (200 g) and sodium acetate (25 g) at room temperature with mechanical stirring. After the addition was completed, the mixture was stirred for 16 h and then diluted with diethyl ether (2 L) and filtered through silica gel in a fritted funnel. The filtrate was concentrated in vacuo and the resulting solid was crytallized from methanol to give the pure ketone 3. Yield: 158.7 g, (87%). $^1$H NMR δ ($CDCl_3$, 300 MHz, TMS): 0.86 (s, 3H, 18$CH_3$), 1.02 (s, 3H, 19$CH_3$), 3.12–3.42 (m, 4H, S$CH_2$), 5.49 (s, 1H, C-4H).

Method B

The thioketal 2 (182.3 g, 0.5 mole) was dissolved in a solution of 4-Methylmorpholine N-oxide (NMO) (87.9 g, 0.75 mole) in dry dichloromethane (1.5 L). 200 g of powdered molecular seives 4A was added. The catalyst Tetrapropylammonium perruthenate (TOAP) (6 g, 3.5 % mole) was added in 1 g portion every 5 min. After 1 hour, starting material was consumed. The solid material was removed by filtration over a short pad of silica gel and 4-Methylmorpholine was removed by washing the filtrate with diluted hydrochloric acid (1N). After drying with $MgSO_4$ the solvent was removed under vacuo. The solid was then dissolved in a minimum (500 mL) of Ethyl acetate/Carbon tetrachloride mixture (4/6). This solution was poured over a silica gel pad and eluted with the same solvent mixture. Evaporation of the solvent and drying gave the ketone 3 (137 g, 75% yield).

Tetrahydropyranyl Ether 4

2-(3-Butynyloxy)tetrahydro-2H-pyran (112.5 g, 0.729 mole) was added dropwise to a solution of methyllithium (500 mL of MeLi 1AM in ether, 0.7 mole) in 1 L of anhydrous THF at −30° C. under argon atmosphere in a 5 L round bottom flask. After this addition was completed, the cooling bath was removed and the solution was allowed to stand at room temperature for 4 hours. The solution was cooled again at −30° C. and a solution of ketone 3 (75 g, 0.2 mole) in 2.5 L of anhydrous TTh was added dropwise. After completing this addition, the cooling bath was removed and the mixture was allowed to stand at room temperature for 16 h. To this mixture, 100 mL of brine were added and the solution was diluted with ethyl acetate, washed with brine and dried with anhydrous $MgSO_4$. The solvent was then evaporated and crystallization took place after a short period of time. Hexane was added to complete the precipitation. The solid was then filtered and washed with hexane. The compound 4 was used in the next step without further purification. Yield: 95.8 g (90%). $^1$H NMR δ (CDCl$_3$, 300 MHz, TMS): 0.82 (s, 3H, 18CH$_3$), 1.01 (s, 3H, 19CH$_3$), 2.52 (t, 2H, J=6.8 Hz, CCCH$_2$), 3.15–3.44 (m, 4H, SCH$_2$), 3.50–3.56 (m, 2H, CH$_2$OTHP), 3.75–3.90 (m, 2H, pyran OCH$_2$), 4.66 (s, 1H, OCHO), 5.47 (s, 1H, C-4H).

Alcohol 5

A mixture of compound 4 (100 g, 0.19 mole) and methyliodide (250 mL, 3.8 moles) in 96% methanol (2.5 L) was heated under reflux for 16 h. The solvent was then removed in vacuo and the crude mixture was diluted with ethyl acetate (2.5 L). The organic phase was then washed with 3% NaOH (3×750 mL) and dried over $MgSO_4$. After evaporation of the solvent, the solid was washed with diethyl ether, filtered on a fritted funnel and washed again with diethyl ether. This compound 5 could be used without further purification in the next step; 45.5 g (66% yield); a sample was recrystallized in a mixture of ethyl acetate and hexane and gave: mp: 179–181° C.; $^1$H NMR δ (CDCl$_3$, 300 MHz, TMS): 0.85 (s, 3H, 18CH$_3$), 1.17 (s, 3H, 19CH$_3$), 2.45 (t, 2H, J=6.0 Hz, CCCH$_2$), 3.70 (t, 2H, J=6.1 Hz, CH$_2$OH), 5.71 (s, 1H, C-4H).

17α-(4'-chlorobutynyl)-17β-hydroxy-4-androsten-3-one (EM 248)

A mixture of alcohol 5 (15 g, 0.04 mole), triphenylphosphine (21 g, 0.08 mole) and carbon tetrachloride (9.3 g, 0.06 mole) was heated under reflux in 1 L of anhydrous dichloromethane for 10 h. After evaporation of the solvent, the crude mixture was adsorbed on silica gel and chromatographied on this gel (flash) with diethyl ether:hexane (70:30). The compound was further purified by crystallization in diethyl ether. Yield 85%; mp: 120–121° C.; $^1$H NMR δ (CDCl$_3$, 300 MHz, TMS): 0.87 (s, 3H, 18CH$_3$), 1.19 (s, 3H, 19CH$_3$), 2.69 (t, 2H, J=7.0 Hz, CCCH$_2$), 3.58 (t, 2H, J=7.0 Hz, CH$_2$Cl), 5.72 (S, 1H, C-4H); HRMS: calcd for $C_{23}H_{31}O_2Cl$: 374.2013; found; 374.20153; Anal. calcd: C, 73.68; H, 8.33; Cl, 9.46.found: C, 73.65; H, 8.45; Cl, 9.58.

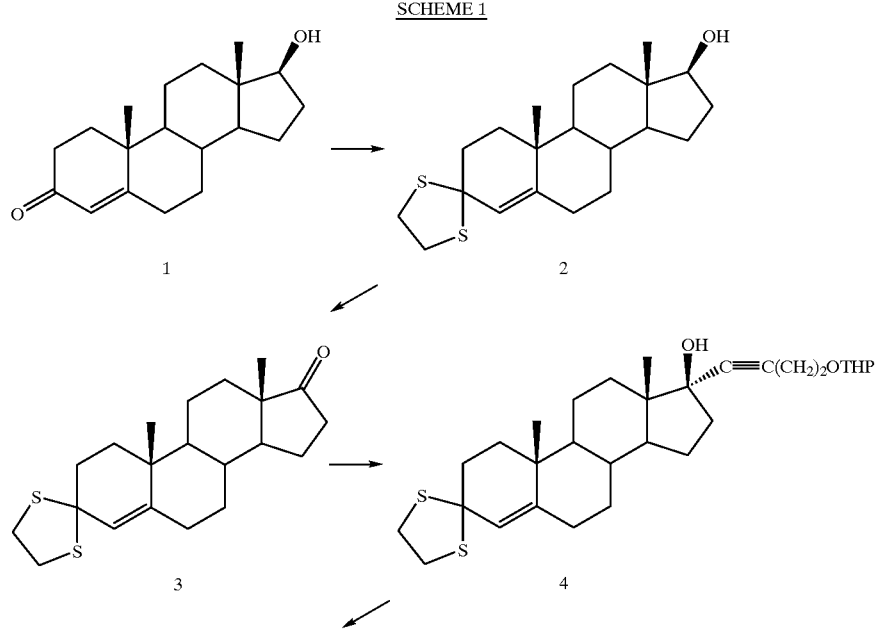

SCHEME 1

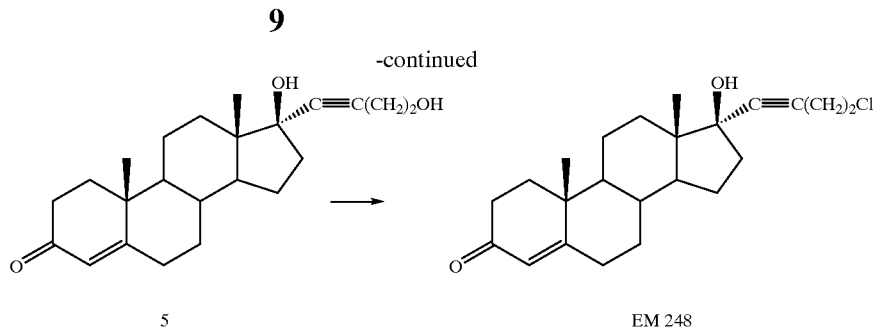

5                                 EM 248

EXAMPLE 2

Syntheses of 17α-(4'-iodobutynyl)-17β-hydroxy-4-androsten-3-one (EM 250)

Synthese A

To a mixture of triphenylphosphine (7.87 g, 30 mmol) and iodine (7.61 g, 30 mmol) in dry dichloromethane (500 mL) was added, at room temperature, imidazole (2.04 g, 30 mmol). After a short period of time, a solid had precipitated. Then, the alcohol 5 (7.13 g, 20 mmol) was added at room temperature. After the mixture was stirred for 30 min., the solution was diluted with ether (100 mL) and the solid then formed was filtered on a fritted funnel. The filtrate was evaporated and the residue was chromatographed on silica gel (flash) with a mixture of diethyl ether and hexane (70/30) as eluant. The compound (EM 250) was further purified by crystallisation in diethyl ether: 6.34 g, 68% yield; m.p.: 124.5–125.5° C.; IR ν cm$^{-1}$ (KBr) 1611, 1653, 2873, 2948, 3380 and 3510; $^1$H NMR δ (CDCl$_3$, 300 MHz, TMS): 0.86 (s, 3H, 18 CH$_3$), 1.17 (s, 3H, 19 CH$_3$), 2.80 (t, 2H, J=7.1 Hz, CCCH), 3.21 (t, 2H, J=7.1 Hz, CH$_2$), 5.71 (s, 1H, C-4H ), $^{13}$C NMR δ (CDCl$_3$, 75 MHz, TMS): 2.5, 12.7, 20.8, 23.2, 23.9, 31.5, 32.7, 33.9, 35.7, 36.3, 38.6. 38.9, 46.8, 49.8, 53.5, 65.8, 79.8, 84.8, 85.7, 123.9, 171.2, 199.5 ; mass spectrum m/e: 467 (M$^+$), 426, 369, 339, 321, 245, 149, 123, 105, 79(100): HRMS: calcd for C$_{23}$H$_{31}$O$_2$I: 466.1369; found: 466.1382; Anal. calcd: C, 59.23; H, 6.70; I, 27.21. Found: C, 59.22; H, 6.55: I, 27.05.

SCHEME 2

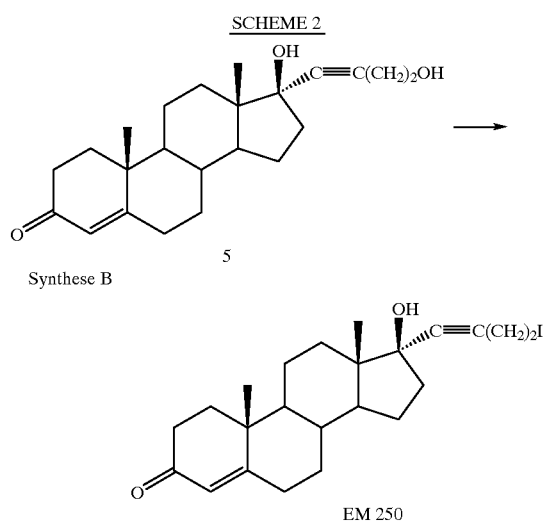

Synthese B

EM 250

3-Methoxyandrosta-3,5-dien-17-one (6)

4-androsten-3,17-dione (15 g, 52 mmol) (available from Aldrich Chemical Company, Milwaukee, Wis., USA) in THF (100 mL) was treated with (MeO)$_3$CH (17 g, 156 mmol) and p-TSA.H$_2$O (450 mg, 2.37 mmol). The mixture was stirred for 2.5 h and treated with Et$_3$N (2.1 mL, 15.6 mmol) and then H$_2$O (4 mL). Removal of the solvent gave wet yellow cake which was stirred with H$_2$O (100 mL) for 10 min and filtered. The solid was washed with water (4 times) and dried at 80° C. in high vacuo for 12 h to give the product (15.6 g, 100%). $^1$H-NMR δ (CDCl$_3$, 300 MHz, TMS): 0.93 (s, 3H, 18-CH$_3$), 0.99 (s, 3H, 19-CH$_3$), 3.57 (s, 3H, OCH$_3$), 5.13 (s, 1H, C$_4$-H), 5.25 (bs, 1H, C$_6$-H); $^{13}$C-NMR δ (CDCl$_3$, 75 MHz, TMS): 220.83, 155.36, 140.92, 117.31, 98.35, 54.20, 51.89, 48.38, 47.58, 35.78, 35.23, 33.68, 31.46, 31.41, 30.66, 25.18, 21.76, 20.44, 18.9, 13.61.

17β-Hydroxy-17α-(4'-hydroxy-butynyl)-4-androsten-3-one (7)

n-Butyllithium (7.9 mL, 19.78 mmol) was added to a mixture of diisopropylamine (0.14 mL, 5% of 19.98 mmol) and 3-butyn-1-ol (15 mL, 19.98 mmol) in THF (30 mL) at −40° C. The mixture was stirred for 1 hour and then chlorotrimethylsilane (2.5 mL, 19.98 mmol) was added and the mixture was stirred for an additional hour (completion of the reaction was checked by NMR). n-BuLi (7.9 mL, 19.78 mmol) was added dropwise. After 1 hour, steroid 6 (2 g, 6.6 mmol) in THF (35 mL) was added and the mixture was stirred for 90 min (TLC showed no starting material ) at −40° C. Water (30 mL) and conc. HCl (3 mL) were added to the mixture and the contents were refluxed for 1 hour (hydrolysis was monitored by TLC). THF was removed and the aq. solution was extracted with CH$_2$Cl$_2$ (5×40 mL). The organic layer was washed successively with sat. NaHCO$_3$ and brine. Drying and removal of the solvents (under water aspirator and then high vacuo) gave the crude product (2.4 g) which was recrystallized with a mixture of n-hexane and ethyl acetate (the contents were kept in the cold room for 24 h before filtration) to give pure product (2.01 g, 85%); $^1$H-NMR δ (CDCl$_3$, 300 MHz, TMS): 0.84 (s, 3H, 18-CH$_3$), 1.16 (s, 3H, 19-CH$_3$), 3.14 (bs, 1H, OH), 3.30 (s, 1H, OH), 3.68 (t, 2H, J=5.87 Hz, CH$_2$OH), 5.71 (s, 1H, C$_4$-H); $^{13}$C-NMR δ (CDCl$_3$, 75 MHz, TMS): 199.58, 171.42, 123.48, 85.71, 82.69, 79.27, 60.75, 53.17, 49.59, 46.35, 38.64, 38.38, 35.96, 35.36, 33.62, 32.54, 32.39, 31.22, 22.87, 22.78, 20.47, 17.13, 12.58.

17β-Hydroxy-17α-(4'-tosyloxy-butynyl)-4-androsten-3-one (8)

In a 100 mL three-necked flask fitted with a stirrer and thermometer were placed 17α-hydroxy-17β-(4-hydroxy-1-butynyl)-androst-4-hen-3-one (4.0 g, 11.22 mmol) and pyridine (10.65 g, 134.64 mmol). The flask was cooled to 0° C. At this temperature, p-toluenesulfonyl chloride (2.35 g, 12.34 mmol) was added in portions over a 20 to 30 min period, or at such a rate that the temperature does not exceed 20° C. at any time. The mixture was then stirred for 12 h at room temperature, after which the mixture was diluted with 30 mL of hydrochloric acid in 70 mL of ice water. The aq. solution was extracted with methylene chloride (3×100 mL). The combined organic phase was washed with brine and dried. Removal of the solvent under water aspirator at 40° C. gave a solid which was dried further in high vacuo for 3 h combined organic phase was washed with 1% aq. sodium bisulfite (80 mL) followed by brine and dried. Removal of the solvent at reduced pressure at 40° C. gave the crude product which was purified by column using hexane/acetone: (4/1), to give the pure product (1.97 g, 95%). Recrystalization with a mixture of hexane and acetone gave the HPLC pure product identical to compound of synthesis A; mp 124.5–125.5° C.

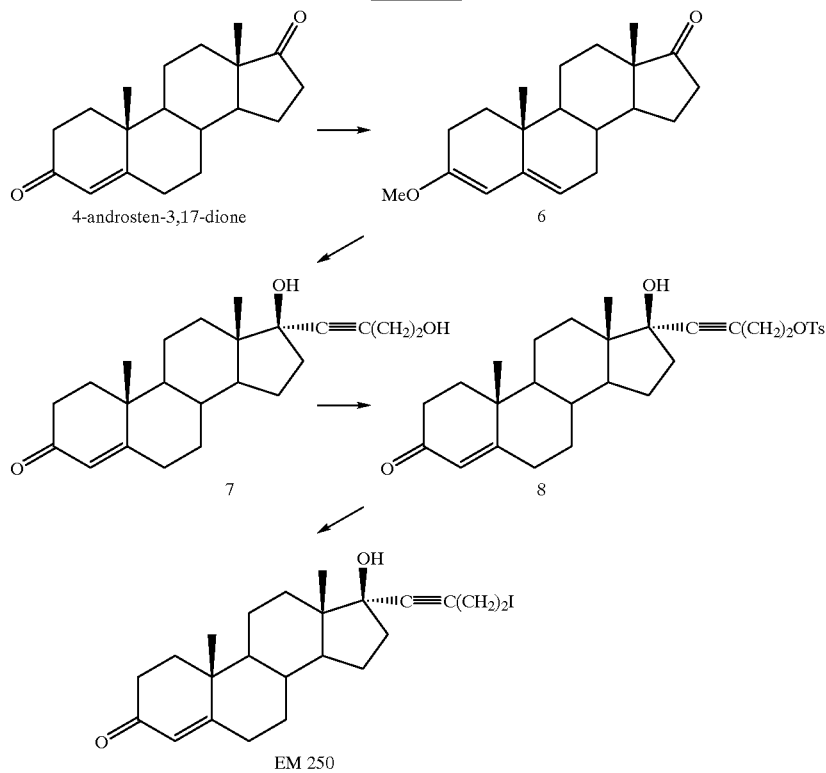

to yield (4.84 g 93%); The anaylsis of $^1$H-NMR spectrum indicated a mixture of tosylate (75%) and chloride (25%). $^1$H-NMR δ (CDCl$_3$, 300 MHz, TMS): 0.84 (s, 3H, 75% 18-CH$_3$), 0.85 (s, 3H, 25% 18-CH$_3$), 1.16 (s, 6H, 2CH3), 2.41 (s, 3H, ArCH$_3$), 257 (t, 2H, J=6.8, 6.8 Hz, 75% CH$_2$), 2.7 (t, 2H, J=6.7, 6.8 Hz, 25% CH$_2$), 3.55 (t, 2H, J=6.7, 6.7 Hz, 25% CH$_2$), 4.06 (t, 2H, J=6.8, 6.8 Hz, 75% CH$_2$), 5.70 (s, 1H, C$_4$H, 731 (d, 2H, J=8.2 Hz, ArH$_2$,H$_6$,), 7.75 (d, 2H, J=8.3 Hz, ArH$_3$,H$_5$,); $^{13}$C-NMR δ (CDCl$_3$, 300 MHz, TMS): 199.6, 171.4, 145.0, 133.0, 129.9, 127.8, 123.8, 86.1, 80.3, 79.6, 67.8, 53.5, 53.2, 49.8, 46.7, 42.1 (C$_4$,Cl) 38.8, 38.6, 36.2, 35.7, 35.6, 33.9, 32.8, 32.5, 315, 31.4, 23.0, 21.7 (ArCH$_3$), 20.7, 19.9, 17.4, 12.8.

17β-hydroxy-17α-(4'-iodo-1-butynyl)-4-androsten-3-one (EM 250)

The above mixture (2.2 g, 4.45 mmol) and NaI (1.33 g, 4.45 mmol) in 2-butanone (12 mL) were refluxed (at 100° C.) for 12 h (after 1 h, TLC indicated the complete conversion of the tosylate to the iodide, however conversion of the chloride to the iodide needed 12 h (NMR)). Removal of the solvent gave the residue which was dissolved in water (50 mL) and extracted with methylene chloride (3×80 mL). The

EXAMPLE 3

In a similar fashion to Examples 1 and 2, the following compounds described in Table 1 are prepared using different tetrahydropyranyloxy-alkynes and different carbon tetrahalides as alkylating reagents.

TABLE 1

| NAME   | X  | n |
|--------|----|---|
| EM 159 | I  | 3 |
| EM 225 | Br | 3 |
| EM 254 | Cl | 3 |
| EM 248 | Cl | 2 |
| EM 249 | Br | 2 |
| EM 250 | I  | 2 |

TABLE 1-continued

[Structure: steroid with OH and C≡C(CH₂)ₙX at 17-position, 4-androsten-3-one core]

| NAME | X | n |
|---|---|---|
| EM 263 | Cl | 1 |
| EM 583 | F | 1 |
| EM 264 | Br | 1 |

EXAMPLE 4

Synthesis of 17β-hydroxy-17α-(4'-iodobut-1'(E)-enyl)-4-androsten-3-one (EM 816)

The ceto enol 6 (300 mg, 1 mmol) and chloromethyl phenyl sulphone (191 mg, 1 mmol) in dry tetrahydrofuran is treated with 1M Potassium t-butoxide (1.3 mL) at room temperature under argon. When the starting material is consumed as shown by t.l.c., water is added and extraction with ether gives the epoxy sulfone 9.

The crude epoxy sulfone 9 (360 mg, 0.8 mmol) in dry tetrahydrofuran under argon is treated with potassium t-butoxide (890 mg, 8 mmol) and water (43 mg, 2.4 mmol) during 2 h at room temperature. The extraction with ether affords the crude hydroxyaldehyde 10 which is dissolved in triethylamine (10 mL), acetic anhydride (150 μL) and 4-(dimethylamino)-pyridine (10 mg). After few days under argon, methanol is added and the mixture is stirred for 30 min. and concentrated in vacuo. The acetoxy aldehyde 11 is extracted with ether and purified by chromatography on "flash" silica-gel using mixture of ethyl acetate and hexane as eluant.

The acetoxy aldehyde 11 (188 mg, 0.5 mmol) in tetrahydrofuran is added under nitrogen to LiBr complex of ylide prepared in situ from 3 bromo-(tetrahydro-2'H-pyran-2'yl) oxy propane, triphenylphosphine, lithium bromide and n-Butyl lithium in the same solvent at low temperature. After few hours, phenyl lithium (0.5 mL) is added followed by t-butyl alcohol and the solution is warmed until completion. Water is added and the adduct 12 is extracted with ether and purified by chromatography on "flash" silica-gel using mixture of ethyl acetate and hexane as eluant.

Potassium t-butoxide (110 mg, 1 mmol) in t-butyl alcohol is added under argon, at 0° C., to a solution of the adduct 12 (350 mg, 0.7 mmol) in dry tetrahydrofuran (5 mL). After stirring for 40 min. the solution is poured into ice-water and extracted with ethyl acetate. The residue is dissolved in methanol (10 mL) and few drops of concentrated HCl is added. The mixture is warmed at reflux for 2 hours, concentrated in vacuo and extracted with ethyl acetate. The cetodiol 13 is purified by chromatography on "flash" silica-gel using mixture of ethyl acetate and hexane as eluant.

To a mixture of triphenylphosphine (196 mg, 0.75 mmol) and iodine (190 mg, 0.75 mmol) in dry dichloromethane (10 mL) is added, at room temperature, imidazole (51 mg, 0.75 mmol). After a short period of time, a solid precipitate. Then, the cetodiol 13 (234 mg, 0.5 mmol) is added at room temperature, the mixture stirred for 30 min. and diluted with ether. The solid thus formed is filtered. The filtrate is evaporated and the residue is chromatographed on silica gel with a mixture of ether and hexane as eluant to give the iodide EM 816.

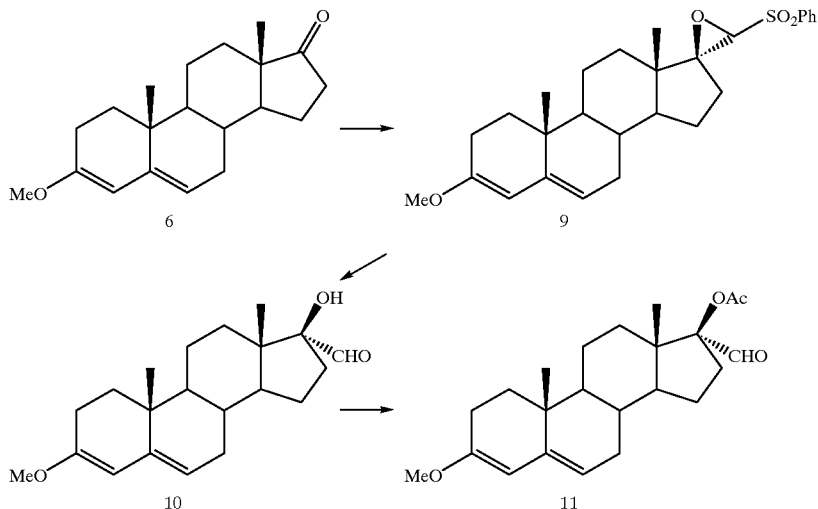

SCHEME 4

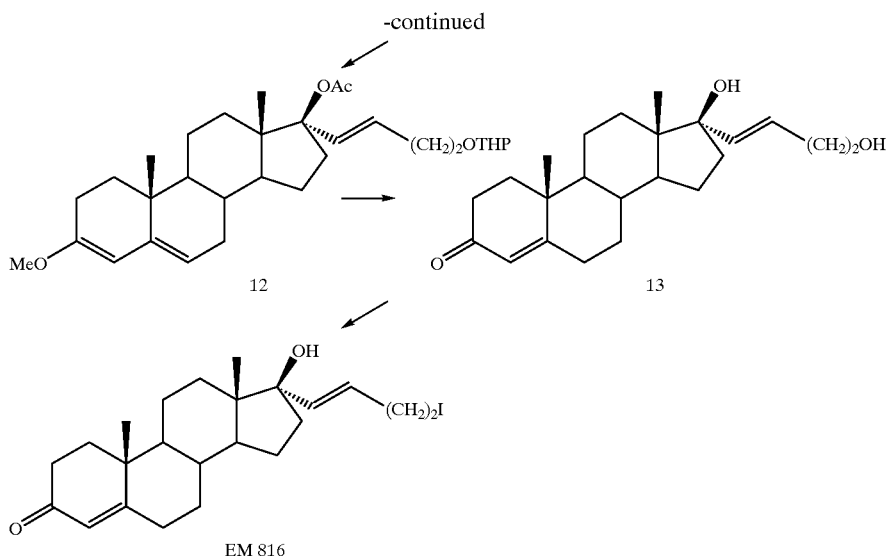

EXAMPLE 5

In a similar fashion to Example 4, the following compounds described in Table 2 are prepared using different bromo-(tetrahydro-2'H-pyran-2'yl)oxy-alkanes or different carbon tetrahalides instead of iodine.

TABLE 2

| NAME | X | n |
|---|---|---|
| EM 810 | Cl | 2 |
| EM 812 | Br | 2 |
| EM 816 | I | 2 |
| EM 850 | Cl | 3 |
| EM 851 | I | 3 |

EXAMPLE 6

Synthesis of 17α-(4'-bromobut-1'(Z)-enyl)-17β-hydroxy-4-androsten-3-one

This is synthesis is described in the scheme 5.

Hydroxy Ketal 14

Testosterone (50 g, 0.17 mol) (available from Schering A.G. Germany) is treated in a apparatus equipped with a Dean-Stark, by diethylene glycol (100 mL) in toluene (1 L) in the presence of a catalytic amount of p-toluenesulfonic acid (1 g) at reflux for 16 h. After cooling and addition of ether, the organic phase is washed with saturated sodium bicarbonate and water, dried and evaporated to give the hydroxy ketal 14.

Cetoketal 15

To hydroxy ketal 14 (40 g, 0.12 mol) in dry methylene chloride (1 L) is added pyridinium dichromate (90 g, 0.24 mol) and the mixture is stirred overnight at room temperature and filtered on 1% triethylamine pretreated silica gel using mixtures of ethyl acetate and hexane as eluant.

Butynyl-adduct 16

In a flame dried flask under an atmosphere of argon is added (tetrahydro-2'H-pyran-2'yl)oxy-butyne (77 g, 0.5 mol) and anhydrous tetrahydrofuran (1 L). The solution is cooled to −78° C. and 2.5N n-BuLi (200 mL) is added and the solution is stirred at this temperature for 2 hours. Then the cetoketal 15 (33 g, 0.1 mol) in tetrahydrofuran (1 L) is added. After 2 hours, water is added and the mixture is warmed to room temperature. The solution is concentrated in vacuo and extracted with ether. The organic phase is washed with water, dried and evaporated. The residue is purified on silica gel using mixture of ethyl acetate and hexane as eluant.

Z-butenyl-adduct 17

To butynyl-adduct 16 (43.7 g, 0.09 mol) dissolved in 500 mL of dry acetone and 120 mL of dry pyridine is added lead poisoned 5% palladium on calcium carbonate (3 g) (Lindlar catalyst, available from Aldrich Chemical Company, Milwaukee, Wis., USA) After three purges with hydrogen, the mixture is stirred under hydrogen at atmospheric pressure during at least 15 min. and then filtered on celite. The solid is washed with a mixture of methanol and methylene chloride and the solvent evaporated. The residue is chromatographed on "flash" silica gel using mixture of ethyl acetate and hexane as eluant.

17α-(4'-bromobut-1'(Z)-enyl)-17β-hydroxy-4-androsten-3-one (18)

Using the procedure described by A. Wagner et al. (Tetrahedron Lettres 30, 557–558, 1989) the tetrahydropyranyloxy group is converted into bromide. Thus $CBr_4$ (31.5 g, 0.095 mol) is added under argon, at room temperature, to a solution of Z-butenyl-adduct 17 (25.2 g, 0.06 mol) in anhydrous methylene chloride (300 mL). After stirring for 10 min. the solution is cooled to 0° C. and triphenyl phosphine (44.5 g, 0.17 mol) is added. The mixture is stirred overnight at room temperature and filtered through silica gel. The solvent is evaporated and the residue is dissolved in a mixture (500 mL) of methanol and water (9:1) and few drop of HCl is added. The mixture is heated few minutes, cooled, evaporated and extracted with ethyl acetate. The organic phase is washed with a saturated solution of sodium bicarbonate and with water, dried and evaporated to dryness. The residue is chromatographed on "flash" silica gel using mixtures of ethyl acetate and hexane as eluant.

EXAMPLE 8

In a similar fashion to Examples 6 and 7, the following compounds described in Table 3 are prepared using different (tetrahydro-2'H-pyran-2'yl)oxy-alkynes or different carbon tetrahalides as reagents.

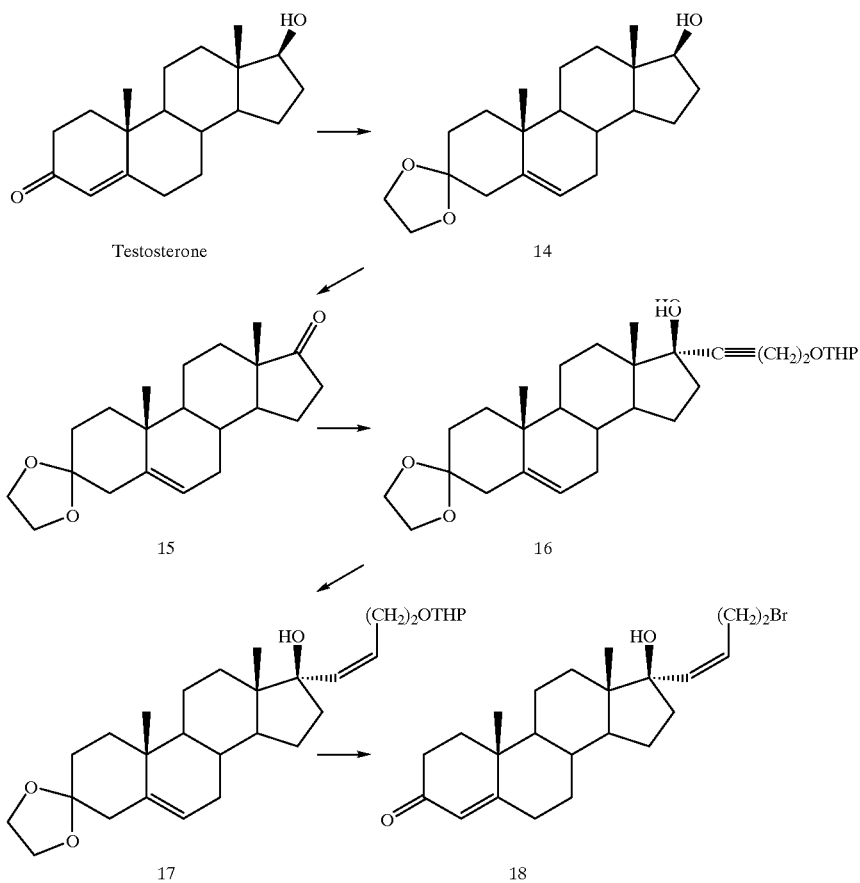

SCHEME 5

EXAMPLE 7

Synthesis of 17α-(4'-iodobut-1'(Z)-enyl)-17β-hydroxy-4-androsten-3-one (19)

The above compound 18 (2.1 g, 5 mmol) and NaI (1.5 g, 5 mmol) in 2-butanone (12 mL) is refluxed for 12 h. Removal of the solvent gives the residue which is dissolved in water (50 mL) and extracted with methylene chloride (3×80 mL). The combined organic phase is washed with 1% aq. sodium bisulfite (80 mL) followed by brine and dried. Removal of the solvent at reduced pressure at 40° C. gives the crude product which is purified by column using a mixture of hexane and acetone as eluant, to give the pure product (4.75 mmol, 95%).

TABLE 3

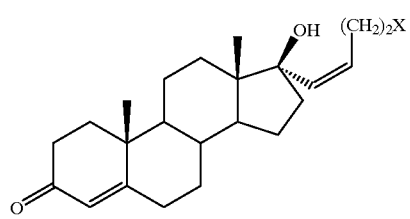

| NAME | X | n |
|---|---|---|
| EM 821 | Cl | 2 |
| EM 831 | Br | 2 |
| EM 817 | I | 2 |
| EM 849 | Cl | 3 |
| EM 848 | I | 3 |

EXAMPLE 9

Synthesis of 17α-(5'-chloropentynyl)-17β-hydroxy-6α-methyl-4-androsten-3-one (EM 339)

This synthesis is described in the scheme 6.

Epoxyde 20

To cetal 14 (40 g, 0.21 mol) in isopropanol (500 mL) was added monoperoxyphtalic acid, magnesium salt (MMPP) (89.6 g, 0.18 mol) in water (250 mL). The mixture was heated at 50° C. for 3 hours and then evaporated and filtrated. The filtrate was extracted with ethyl acetate and the organic phase was washed with water, dried and evaporated. The residue was chromatographed on "flash" silica gel with a mixture of ethyl acetate and hexane (4:6) to give the β-isomer (20 g) and the α-isomer (17 g).

Cetoalcohol 21

To methylmagnesium chloride (20 mL, 6M in THF) was added dropwise under argon, the α-isomer of epoxyde 20 (7.0 g, 0.02 mol) in anhydrous ether (250 mL). The mixture was heated at reflux for 1 hour and stirred at room temperature for 3 hours and ammonium chloride was added. The mixture was extracted with diethyl ether. The organic phase was washed with water, dried and evaporated to dryness.

To the residue dissolved in dry methylene chloride (400 mL) was added celite (18 g) and pyridinium dichromate (18 g) and the mixture was stirred at room temperature for 24 hours. The reaction mixture was then poured into diethyl ether and filtered through florisil covered by a layer of celite. The evaporation of the solvent gave crude cetoalcohol 21 which was purified by chromatography on "flash" silica gel with a mixture of ethyl acetate and hexane (4:6).

Adduct 22

2-(4-pentynyloxy)tetrahydro-2H-pyran (13.8 g, 0.083 mole) was added dropwise to a solution of methyllithium (59 mL of MeLi 1.4M in ether, 0.08 mole) in 200 mL of anhydrous THF at −60° C., under argon atmosphere, in a 1 L round bottom flask. After this addition was completed, the cooling bath was removed and the solution was allowed to stand for 5 hours. The solution was cooled again at −60° C. and a solution of cetoalcohol 21 (6 g, 0.017 mole) in 150 mL of anhydrous THF was added dropwise. After completing this addition, the cooling bath was removed and the mixture was allowed to stand at room temperature for 16 h. To this mixture, 20 mL of brine were added and the solution was diluted with ethyl acetate, washed with brine and dried with anhydrous $MgSO_4$. The solvent was then evaporated and the residue was purified by chromatography on "flash" silica gel with mixtures of ethyl acetate and hexane (0:10 to 4:6) to give the adduct 22 (7.5 g, 0.014 mol).

Cetotriol 23

The adduct 22 (6.2 g, 12 mmol.) was dissolved in a mixture of acetic acid, acetone, THF and water (4:2:2:1) and heated at reflux for 24 hours. Then the mixture was concentrated at the half of the volume, cooled and extracted with ethyl acetate. The organic phase was washed with brine, dried and evaporated. The recrystallisation of the residue with a mixture of benzene and hexane gave pure cetotriol 23 (3.1 g, 7.7 mmol.).

Enonediol 24

To cetotriol 23 (1.0 g, 2.8 mmol.) dissolved in methanol (150 mL) was added 0.1M NaOH (10 mL) and the solution was heated at 50° C. for 24 hours. After neutralisation with dilute hydrochloric acid, water was added and the mixture was extracted with ethyl acetate. The organic phase was washed with water, dried and evaporated to dryness. The residue was purified by chromatography on "flash" silica gel using mixtures of acetone and hexane (0:10 to 2:8) as eluant to give enonediol 24 (784 mg, 2.0 mmol.): m.p. 153–154° C.

17α-(5'-chloropentynyl)-17β-hydroxy-6α-methyl-4-androsten-3-one (EM 339)

A mixture of enonediol 24 (102 mg, 0.27 mmol.), triphenylphosphine (131 mg, 0.5 mmol.) and carbon tetrachloride (40 mg, 0.26 mmol.) was heated under reflux in 20 mL of anhydrous dichloromethane for 10 h. After evaporation of the solvent, the crude mixture was adsorbed on "flash" silica gel and eluted with mixtures of ethyl acetate and hexane (0:10 to 3:7) to give EM 339 (66 mg, 0.16 mmol); m.p. 56–58° C.; IR ν $cm^{-1}$ (KBr) 1606.4, 1663.1, 2871.9, 2947.6 and 3414.4; $^1H$ NMR δ ($CDCl_3$, 300 MHz, TMS): 0.88 (s, 3H, 18-$CH_3$), 1.07 (d, 3H, J=6.43 Hz, 6-$CH_3$) 1.19 (s, 3H, 19-$CH_3$), 2.42 (t, 2H, J=6.85 Hz, $CCCH_2$), 3.63 (t, 2H, J=6.37 Hz, $CH_2Cl$), 5.79 (S, 1H, C-4H); $^{13}C$ NMR δ ($CDCl_3$, 75 MHz, TMS): 12.8, 16.3, 18.4, 20.9, 23.0, 31.4, 32.7, 33.7, 33.8, 36.0, 36.1, 39.0, 39.2, 40.6, 43.6, 46.8, 49.9, 53.8, 77.2, 79.8, 84.4, 1213, 174.2 and 199.8; mass spectrum m/e: 402 ($M^+$), 369, 259, 137, 105, 91(100), 79, 67, 55.

SCHEME 6

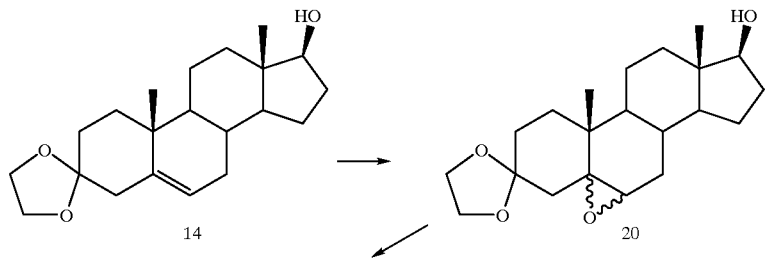

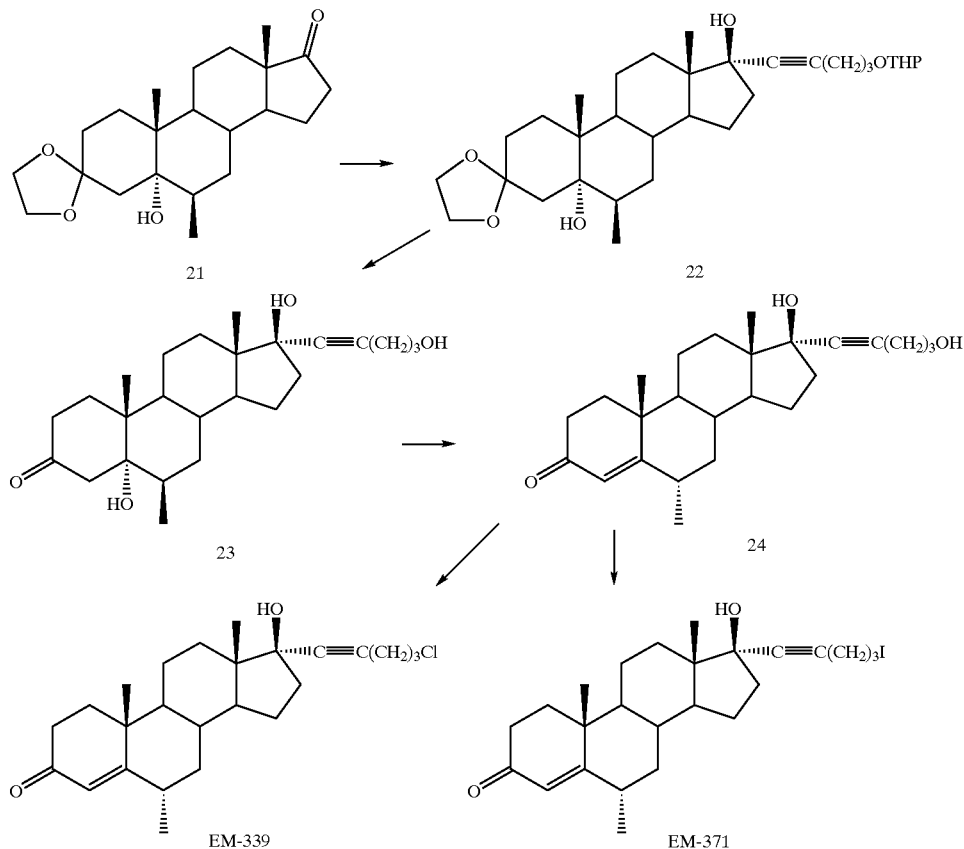

EXAMPLE 10

Synthesis of 17α-(5'-iodopentynyl)-17β-hydroxy-6α-methyl-4-androsten-3-one (EM 371)

17α-(5'-bromopentynyl)-17β-hydroxy-6α-methyl-4-androsten-3-one (EM 304)

This compound was prepared in a similar fashion to example 9 using carbon tetrabromide instead carbon tetrachloride. IR ν cm$^{-1}$ (KBr) 1600, 1650, 2890, 2950 and 3400; $^{1}$H NMR δ (CDCl$_3$, 300 MHz, TMS): 0.88 (s, 3H, 18-CH$_3$), 1.07 (d, 3H, J=6.44 Hz, 6-CH$_3$) 1.20 (s, 3H, 19-CH$_3$), 2.42 (t, 2H, J=5.28 Hz, CCCH$_2$), 3.50 (t, 2H, J=4.98 Hz, CH$_2$Br), 5.79 (s, 1H, C-4H); $^{13}$C NMR δ (CDCl$_3$, 75 MHz, TMS): 12.8, 17.5 18.3, 20.9, 23.0, 31.4, 32.3, 326, 33.6, 33.8, 35.9, 36.0, 38.9, 39.1, 40.5, 43.6, 46.7, 49.8, 53.7, 79.7, 84.2, 121.2, 174.4 and 199.8; mass spectrum m/e: 448, 446 (M$^+$), 433, 431, 340, 259, 137 (100), 91, 55.

17α-(5'-iodopentynyl)-17β-hydroxy-6α-methyl-4-androsten-3-one (EM-371)

To EM-304 (140 mg, 0.32 mmol.) in acetone (20 mL) was added NaI (75 mg, 0.5 mmol.) and the mixture was heated at reflux overnight. After cooling and removal of the solvent, water was added and the mixture extracted with ethyl acetate. The organic phase was washed with 1% sodium bisulfite and water, dried, and evaporated to dryness. The residue was purified by chromatography on "flash" silica gel using mixtures of acetone and hexane (0:10 to 1:9) to give EM-371 (79 mg, 0.16 mmol.): m.p. 68–70° C.; IR ν cm$^{-1}$ (KBr) 1605.9, 1683.1, 29413 and 3423.3; $^{1}$H NMR δ (CDCl$_3$, 300 MHz, TMS): 0.87 (s, 3H, 18-CH$_3$), 1.06 (d, 3H, J=632 Hz, 6-CH$_3$), 1.18 (s, 3H, 19-CH$_3$), 1.96 (q, 2H, J=6.7Hz, CH—$_2$CH$_2$I), 3.27 (t, 2H, J=6.80 Hz, CH$_2$I), 5.78 (s, 1H, C-4H); $^{13}$C NMR δ (CDCl$_3$, 75 MHz, TMS): 5.2, 12.8, 18.3, 19.8, 20.9, 22.9, 29.6, 313, 31.8, 32.6, 33.6, 33.7, 35.9, 36.0, 38.9, 39.1, 40.5, 46.8, 49.2, 53.7, 79.7, 84.8, 121.2, 174.3, 199.8; mass spectrum m/e: 494 (M$^+$), 479, 367, 300, 259, 137, 105, 91, 79, 67 (100), 55.

TABLE 4

| NAME | X | n |
|------|---|---|
| EM-304 | Br | 3 |
| EM-371 | I | 3 |

EXAMPLE 11

Synthesis of 17α-(5'-chloropentynyl)-17β-hydroxy-6-methyl-androsta-4,6-dien-3-one (EM 683)

To EM-339 (100 mg, 0.25 mmol.) in benzene (20 mL) was added p-toluene sulfonic add (4.72 mg, 0.025 mmol)

and chloranile (74 mg, 0.29 mmol). The mixture was heated with a Dean-Stark at reflux during 2 hours. After cooling, ether was added and the organic phase was washed with NaHS$_2$O$_3$ and water, dried on MgSO$_4$ and evaporated to dryness. The residue was chromatographed on "flash" silica gel using a mixture of ethyl acetate and hexane as eluant to give the desired compound (48 mg, 48% yield): IR v cm$^{-1}$ (KBr) 1070, 1577, 1624, 2870, 2943 and 3421; $^1$H NMR δ (CDCl$_3$, 300 MHz, TMS):0.92 (s, 3H, 18-CH$_3$), 1.09 (s, 3H, 19-CH$_3$), 1.83 (s, 3H, 6-CH$_3$), 1.95 (q, 2H, J=6.53 Hz, CH$_2$CH$_2$Cl), 2.41 (t, 2H, J=6.87 Hz, CCCH$_2$), 3.62 (t, 2H, J=632 Hz, CH$_2$Cl), 5.86 (s, 1H, C-4H), 5.94 (s, 1H, C-7H ). $^{13}$C NMR δ (CDCl$_3$, 75 MHz, TMS): 12.7, 163, 16.4, 19.9, 20.4, 22.6, 31.4, 32.6, 33.6, 34.1, 36.2, 37.8, 39.1, 43.7, 47.6, 47.9, 50.6, 79.5, 84.3, 84.4, 121.1, 131.1, 138.1, 164.4, 200.

EXAMPLE 12

In a similar fashion to Example 11, the following compounds described in Table 5 are prepared using different compounds synthesized according the examples 9 and 10 as starting material.

TABLE 5

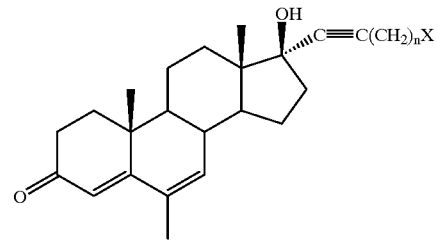

| NAME | X | n |
|---|---|---|
| EM 902 | Cl | 2 |
| EM 832 | Br | 2 |
| EM 911 | I | 2 |
| EM 789 | Br | 3 |
| EM 834 | I | 3 |

EXAMPLE 13

Synthesis of 17α-(but-3-en-1-ynyl)-17β-hydroxy-4-androsten-3one (EM 656)

To EM-250 (466 mg, 1 mmol) in benzene (25 mL) was added cesium fluoride (759 mg, 5 mmol). The mixture was stirred at room temperature for 24 hours, then washed with water, dried and evaporated to dryness. The residue was chromatographed on "flash" silica gel using a mixture of diethyl ether and hexane (6:4) as eluant to give the desired compound (186 mg. 0.55 mmol): $^1$H NMR δ (CDCl$_3$, 300 MHz, TMS): 0.90 (s, 3H, 18-CH$_3$), 1.20 (s, 3H, 19-CH$_3$), 5.46 (dd, 1H, J=10.97 Hz, J=1.82 Hz, =CH$_2$), 5.61 (dd, 1H, J=17.4 Hz, =CH$_2$), 5.73 (s, 1H, C-4H), 5.83 (dd, 1H, J=17.4 Hz, J=10.97 Hz, CH=CH$_2$).

EXAMPLE 14

Synthesis of 17α-(pent-4-en-1-ynyl)-17β-hydroxy-4-androsten-3-one

This compound is prepared from EM-159 by a technique similar to those described in example 13.

EXAMPLE 15

Synthesis of 17α-(4'-iodobutyl)-17β-hydroxy-4-androsten-3one (29)

This synthesis is described in the scheme 7.

Hydroxy Ketal 25

Androstanolone (50 g, 0.17 mol) (available from Aldrich Chemical Company, Inc, Milwaukee Wis. USA) is treated in a apparatus equipped with a Dean-Stark, by diethylene glycol (100 mL) in toluene (1 L) in the presence of a catalytic amount of p-toluenesulfonic acid (1 g) at reflux for 16 h. After cooling and addition of ether, the organic phase is washed with saturated sodium bicarbonate and water, dried and evaporated to give the hydroxy ketal 25.

Cetoketal 26

To hydroxy ketal 25 (40 g, 0.12 mol) in dry methylene chloride (1 L) is added pyridinium dichromate (90 g, 0.24 mol) and the mixture is stirred overnight at room temperature and filtered on 1% triethylamine pretreated silica gel using mixtures of ethyl acetate and hexane as eluant.

Butynyl-adduct 27

In a flame dried flask under an atmosphere of argon is added (tetrahydro-2'H-pyran-2'yl)oxy-butyne (77 g, 0.5 mol) and anhydrous tetrahydrofuran (1 L). The solution is cooled to −78° C. and 2.5N n-BuLi (200 mL) is added and the solution is stirred at this temperature for 2 hours. Then, the cetoketal 26 (33 g, 0.1 mol) in tetrahydrofuran (1 L) is added. After 2 hours, water is added and the mixture is warmed to room temperature. The solution is concentrated in vacuo and extracted with ether. The organic phase is washed with water, dried and evaporated. The residue is purified on silica gel using mixture of ethyl acetate and hexane as eluant.

Ceto-alcohol 28

To butynyl-adduct 27 (43.7 g, 0.09 mol) dissolved in 500 mL of ethanol is added 5% palladium on charcoal. After three purges with hydrogen, the mixture is stirred under hydrogen at medium pressure during at least 60 min. and then filtered on celite. The solid is washed with a mixture of methanol and methylene chloride and the solvent evaporated. The residue is dissolved in methanol and few drops of concentrated HCl, and heated at reflux for 1 hour. After cooling and evaporation of a part of the solvent, the ceto-alcohol 28 is extracted with ethyl acetate, washed with water, dried and purified by chromatography on "flash" silica gel using mixture of ethyl acetate and hexane as eluant.

17α-(4'-iodobutyl)-17β-hydroxy-4-androsten-3-one (29)

To a stirred solution Ceto-alcohol 28 (1.8 g, 5 mmol) in dimethyl formamide (50 mL) containing a catalytic amount of p-toluenesulfonic add monohydrate (100 mg, 0.5 mmol.) is added, at room temperature, bromide (880 mg, 5.5 mmol.) in same solvent (10 ml) over a period of 8 hours. The mixture is poured in water and extracted with ethyl acetate. The organic phase is washed with 1% aq. sodium bisulfite and with water, dried and evaporated. To the residue dissolved in dimethyl formamide (50 mL) is added lithium carbonate (1.0 g) and lithium bromide (1.0 g) and the mixture is heated at reflux for few hours. After cooling, the mixture is poured in water and extracted with ethyl acetate. The organic phase is washed with 1% aq. sodium bisulfite and with water, dried and evaporated. The residue is purified by chromatography on "flash" silica gel using mixtures of ethyl acetate and hexane as eluant. The purified enone-alcohol thus obtained is then added at room temperature to a mixture of triphenylphosphine (1.3 g, 5 mmol.), iodine (1.26 g, 5 mmol.) and imidazole (0.34 g, 5 mmol.). The mixture is stirred for 30 min. and then diluted with ether. The solid then formed is filtered on a fritted funnel. The filtrate is evaporated and the residue is chromatographed on "flash" silica gel using mixtures of ethyl acetate and hexane as eluant.

funnel. The filtrate was concentrated in vacuo and the residue was purified by chromatography on "flash" silica gel with mixtures of ethyl acetate and hexane to give the fluoroalcohol 31 (270 mg, 84% yield).

Fluorodiol 32

2-(4-pentynyloxy)tetrahydro-2H-pyran (4.61 g, 0.027 mole) was added dropwise to a solution of methyllithium (19.6 mL of MeLi 1.4M in ether, 0.028 mole) in 100 mL of anhydrous THF at −78° C. under argon atmosphere in a 0.5

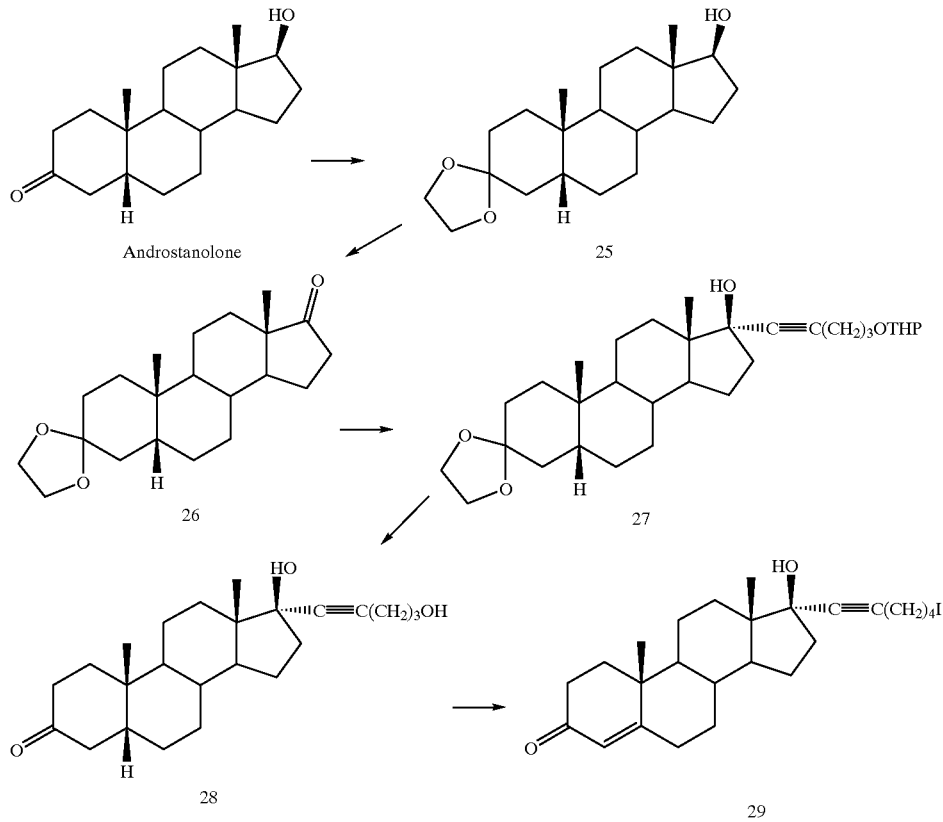

SCHEME 7

EXAMPLE 16

Synthesis of 17α-(5'-chloropentynyl)-17β-hydroxy-6-fluoro-4-androsten-3-one (EM 649)

This synthesis is described in the scheme 8.

Fluoroketal 30

To α-isomer of epoxyde 20 (1 g, 2.9 mmol.) in an anhydrous mixture of ether and benzene (1:1) was added BF$_3$OEt$_2$ (1 mL) at 5 to 10° C. and the mixture was stirred at room temperature for 3 hours. The organic phase was washed with saturated solution of sodium bicarbonate and with water, dried and evaporated to give a white solid (380 mg, 36% yield).

Fluoroalcohol 31

A solution of fluoroketal 30 (320 mg, 0.87 mmol.) in dry dichloromethane (15 mL) was added dropwise to a solution of pyridinium chlorochromate (0.6 g, 0.7 mole), molecular sieves 3A (0.5 g) and sodium acetate (100 mg) at room temperature with stirring. After the addition was completed, the mixture was stirred for 16 h and then diluted with diethyl ether (100 mL) and filtered through silica gel in a fritted L round bottom flask. After this addition was completed, the cooling bath was removed and the solution was allowed to stand for 2 hours. The solution was cooled again at −78° C. and a solution of fluoroalcohol 31 (2 g, 5.48 mmole) in 100 mL of anhydrous THF was added dropwise. After completing this addition, the cooling bath was removed and the mixture was allowed to stand at room temperature for 16 h. To this mixture, 20 mL of brine were added and the solution was diluted with ethyl acetate, washed with brine and dried with anhydrous MgSO$_4$. The solvent was then evaporated and the residue was purified by chromatography on "flash" silica gel with mixtures of ethyl acetate and hexane (0:10 to 4:6) to give the fluorodiol 32.

Fluorotriol 33

To a mixture of fluorodiol 32 (410 mg, 0.776 mmol.), acetic acid (40 mL), THF (20 mL), acetone (20 mL) and water (10 mL) was heated at reflux for 8 hours. After cooling, the mixture was poured in water and extracted with ethyl acetate. The organic phase was washed with saturated aq. solution of sodium bicarbonate and with water, dried and evaporated. The residue was chromatographed on "flash" silica gel using mixtures of acetone and hexane as eluant to give the fluorotriol 33 (181 mg, 57% yield).

17α-(5'-chloropentynyl)-17β-hydroxy-6-fluoro-4-androsten-3-one (EM 649)

A mixture of fluorotriol 33 (100 mg, 0.246 mmol.), triphenylphosphine (129 mg, 0.492 mmol.) and carbon tetrachloride (5 mL) was heated under reflux in 20 mL of anhydrous dichloromethane for 3 h. After evaporation of the solvent, the crude mixture was adsorbed on silica gel and chromatographied on this gel (flash) with acetone/hexane (0:10 to 3:7); IR ν cm$^{-1}$ (KBr), 1670, 2943 and 3433; $^1$H NMR δ (CDCl$_3$, 300 MHz, TMS): 0.91 (s, 3H, 18-CH$_3$), 132 (d, 3H, J=1.5 Hz, 19-CH$_3$), 1.96 (q, 2H, J=6.5 Hz, CH$_2$CH$_2$CL), 2.43 (t, 2H, J=6.9 Hz, CCCH$_2$), 3.64 (t, 2H, J=6.5 Hz, CH$_2$Cl), 4.99 (d, 1H, J=49.1 Hz, C-6H), 5.88 (d, 1H, J=4.8 Hz, C-4H).

EXAMPLE 18

Synthesis of 17α-(4'-iodobutynyl)-17β-hydroxy-4-methyl-4-androsten-3-one

This compound is prepared by a method similar to the preparation of 17α-(4'-iodobutynyl)-17β-hydroxy-4-androsten-3-one (EM 250) described in Synthesis B of the Example 2 using 4-methyl-4-androsten-3,17-dione instead of 4-androsten-3,17-dione as starting material.

The synthesis of 4-methyl-4-androsten-3,17-dione may be made as follow:

A mixture of Testosterone acetate (available from Steraloids Inc, Wilton, N.H. USA) (3.3 g, 10 mmol.), aqueous formaldehyde (1 mL) and thiophenol (0.9 g, 8 mmol ) is

SCHEME 8

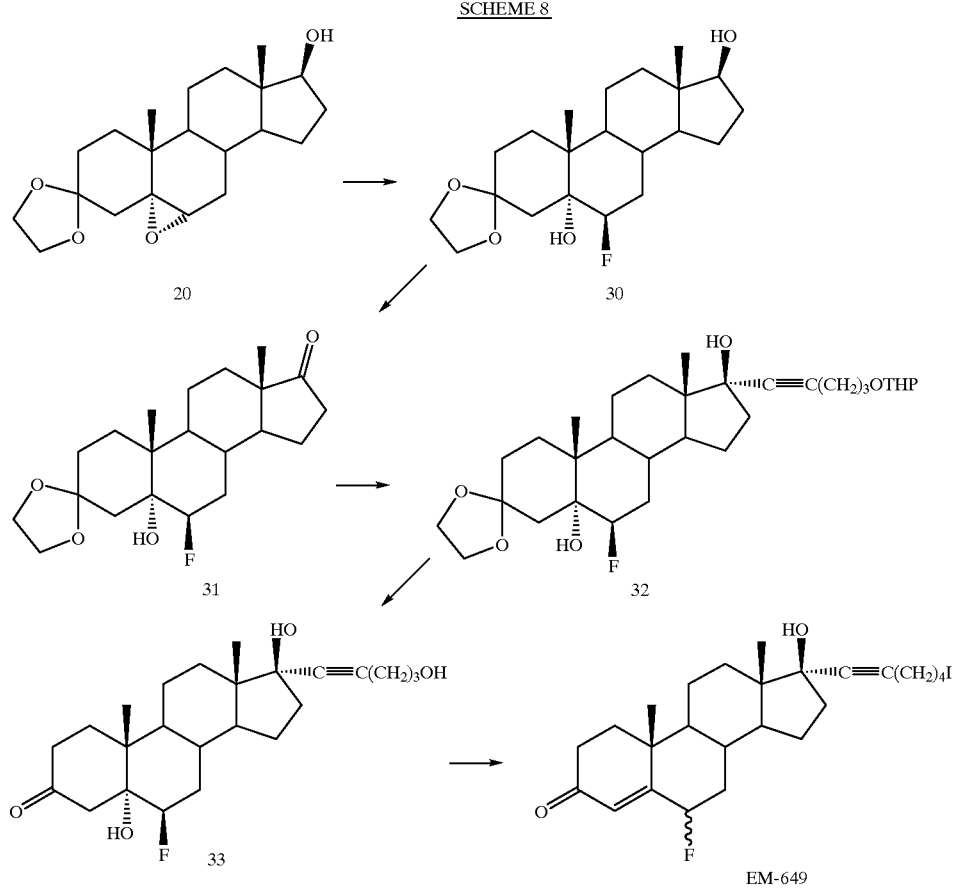

EXAMPLE 17

Synthesis of 17α-chlorobutynyl)-17β-hydroxy-androsta-1,4-diene

A mixture of EM-248 (187 mg, 0.5 mmol.), DDQ (170 mg, 0.75 mmol. diclhlorodicyanobenzoquinone), p-nitrophenol (5 mg) and toluene (3 mL) was heated for 12 hours. After cooling, ether (150 mL) was added and the solution was washed with NaHSO$_3$, 1N NaOH and water, dried and evaporated. The residue was purified by chromatography on "flash" silica gel using a mixture of ether and hexane (7:3) as eluant. Recrystallisation gave the compound (56 mg, 30% yield).

stirred in triethanolamine (30 mL) for 10 h under an atmosphere of argon at 110° C. After 4 h. additional aqueous formaldehyde (0.7 mL) and thiophenol (0.5 mg) are added. After cooling, the mixture is poured in brine and extracted with methylene chloride. The organic phase is washed with dilute sodium hydroxide solution and with water, dried and evaporated. The residue is purified by chromatography on "flash" silica gel using mixtures of ethyl acetate and hexane as eluant. The purified residue in acetone (15 mL) is added to Raney nickel (35 g) in acetone (60 mL) which is heated at reflux since 1 h. The reflux is continued for 15 min. The hot organic phase is decanted and the metal is washed with hot acetone. The combined filtrates were concentrated and purified by chromatography on "flash" silica gel using a mixture of ethyl acetate and hexane as eluant. The purified residue is dissolved in methanolic potassium hydroxide solution (50 mL, 3%) and kept at room temperature for 4 h. under an atmosphere of argon. After concentration, the mixture is poured in water and extracted with methylene chloride. The organic phase is washed with brine, dried and evaporated to dryness. The residue, purified by chromatography on "flash" silica gel using a mixture of ethyl acetate and hexane as eluant, is dissolved in acetone (30 mL) and treated at 0° C. with a slight excess of Jones' reagent (8N chromium trioxide)(until a red color). After 15 min., isopropanol (1 mL) is added and the mixture is poured in brine and extracted with ethyl acetate. The organic phase is washed with brine, dried and evaporated to dryness. Purification of the residue by chromatography on "flash" silica gel using a mixture of ethyl acetate and hexane as eluant give pure 4-methyl-4-androsten-3,17-dione.

PRODRUGS

Prodrug forms of antiandrogens in accordance with the present invention may be made, in accordance with known technique for modifying substituents of compounds into moieties which convert in vivo back to the unmodified substituent (see e.g. H. Bundgaard, Design and application of prodrugs. In A textbook of Drug Design and Development. Edited by P. Krogsgaard-Larsen and H. Bundgaard. Harwood Academic Publishers GmfH, Chur, Switzerland, 1991, pp. 113–191). In certain preferred embodiments prodrugs are formed, for example, by transforming of the 3-keto group of antiandrogens of the invention into oxazolidines, thiazolidines, dioxanes, dioxolanes, dithiolanes or dithianes. All are unstable in the body and regenerate the corresponding 3-keto compounds.

Non-limiting examples of some preferred prodrug modifications which may be applied to the antiandrogens of the invention are described below.

EXAMPLE 19

17α-(4'-chlorobutynyl)-17β-hydroxy-5-androstene-3-spiro-2'-(1',3'-thiazolidine-4'-ethyl carboxylate) (34)

This synthesis is described in scheme 9.

17α-(chlorobutynyl)-17β-hydroxy-4-androsten-3-one (EM-248) (0.37 g, 1 mmol) is dissolved, under argon, in pyridine (5 mL) to which is added L-cysteine ethyl ester hydrochloride. The reaction mixture is heated at least fo 12 hours. Excess of pyridine is evaporated and the residue dissolved in methylene chloride. The organic solution is washed with water, dried with magnesium sulfate and evaporated to give 17α-(4'-chlorobutynyl)-17β-hydroxy-5-androstene-3-spiro-2'-(1',3'-thiazolidine-4'-ethyl carboxylate).

SCHEME 9

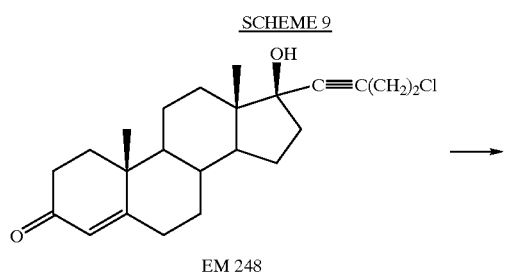

EM 248

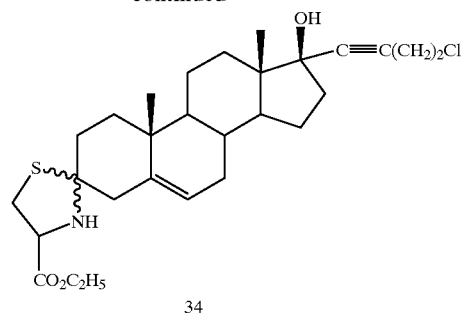

34

EXAMPLE 20

17α-(4'-chlorobutynyl)-17β-hydroxy-5-androstene-3-spiro-2'-(1',3'-oxazolidine-4'-ethyl carboxylate) (35)

This synthesis is described in the scheme 10.

EM-248 (3.7 g, 10 mmol) is dissolved in anhydrous ethanol, sodium acetate is added followed by L-serine ethyl ester hydrochloride (17 g, 100 mmol) and the mixture is heated overnight under an argon atmosphere. The reaction mixture is then evaporated under vacuum. Methylene chloride is added to precipitate excess of L-serine ethyl ester hydrochloride. The solution is then filtered and the filtrate is washed twice with water, dried on magnesium sulfate, filtered and evaporated under vacuum. The residue is triturated with ethanol to give crystals.

SCHEME 10

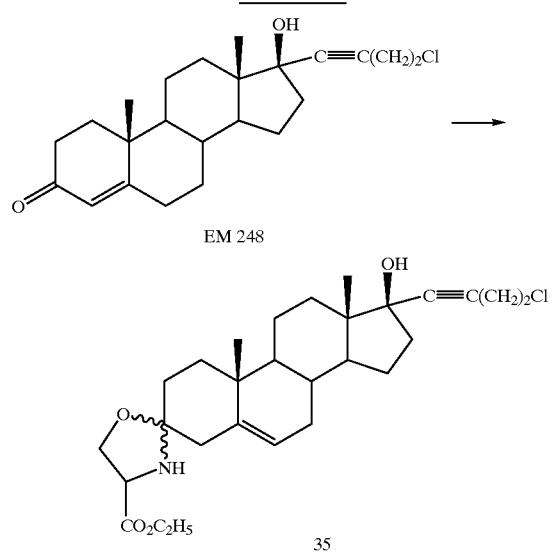

EXAMPLE 21

Synthesis of 17α-(4'-iodobutynyl)-17β-hydroxy-3,3-methylethylenedioxy-5-androstene (38)

This synthesis is described in the scheme 11.

Ketaldiol 36

To the Alcohol 5 (3.75 g, 10 mmol) in benzene (100 mL) and propylene glycol (20 mL) (racemic mixture or preferably pure enantiomer can be used) is added p-toluenesulfonic acid (189 mg, 2 mmol.) and the mixture is heated at reflux with a Dean-Stark apparatus for 24 hours. After cooling, the mixture diluted with ether is washed with a saturated sodium bicarbonate solution and with water, dried and concentrated to dryness in vacuo to give the crude ketaldiol 36.

Ketaltosylate 37

In a 100 mL threenecked flask fitted with a stirrer and thermometer is placed ketaldiol 36 (3.46 g, 8 mmol) and pyridine (7.9 g, 100 mmol). The flask is cooled to 0° C. At this temperature, p-toluenesulfonyl chloride (1.7 g, 9 mmol) is added in portions over a 20 to 30 min period, or at such a rate that the temperature does not exceed 20° C. at any time. The mixture is then stirred for 12 h at room temperature, after which the mixture is diluted with 20 mL of hydrochloric acid in 70 mL of ice water. The aq. solution is extracted with methylene chloride. The organic phase is washed with brine and dried. Removal of the solvent at 40° C. gives the ketaltosylate 37.

17α-(4'-iodobutynyl)-17β-hydroxy-3,3-methylethylenedioxy-5-androstene (38)

The ketaltosylate 37 (2.62 g, 4.45 mmol) and NaI (1.33 g, 4.45 mmol) in 2-butanone (12 mL) is refluxed for 12 h. Removal of the solvent gives the residue which is dissolved in water (50 mL) and extracted with methylene chloride. The organic phase is washed with 1% aq. sodium bisulfite (80 mL) followed by brine and dried. Removal of the solvent at reduced pressure at 40° C. gives the crude product which is purified by chromatography on 0.1% triethylamine pretreated "flash" silica gel using mixture of ethyl acetate and hexane as eluant.

EXAMPLE 22

Synthesis of 17α-(4'-iobutynyl)-17β-hydroxy-3-ethoxy-androsta-3,5-diene (40)

17α-(4'-chlorobutynyl)-17β-hydroxy-3-ethoxy-androsta-3,5-diene (39)

EM-248 (1.9 g, 5 mmol) in TBF (20 mL) is treated with (Eto)3CH (1.7 g, 16 mmol) and p-Toluenesulfonic acid monohydrate (45 mg, 0.24 mmol). The mixture is stirred for 2.5 h and treated with Et₃N (0.2 mL, 1.6 mmol) and then H₂O (0.5 mL). Removal of the solvent gives a residue which is stirred with H₂O (20 mL) for 10 min and filtered. The solid was washed with water and dried at 80° C. in high vacuo to give crude compound 39. Pure product is obtained by chromatography on 0.1% triethylamine pretreated flash" silica gel using mixture of ethyl acetate and hexane as eluant.

17α-(4'-iodobutynyl)-17β-hydroxy-3-ethoxy-androsta-3,5-diene (40)

The compound 39 (800 mg, 2 mmol) and NaI (580 mg, 2 mmol) in 2-butanone (12 mL) is refluxed for 12 h. Removal of the solvent gives the residue which is dissolved in water (50 mL) and extracted with methylene chloride. The organic phase is washed with 1% aq. sodium bisulfite (80 mL) followed by brine and dried. Removal of the solvent at reduced pressure at 40° C. gives the crude product which is purified by chromatography on 0.1% triethylamine pretreated "flash" silica gel using mixture of ethyl acetate and hexane as eluant.

SCHEME 11

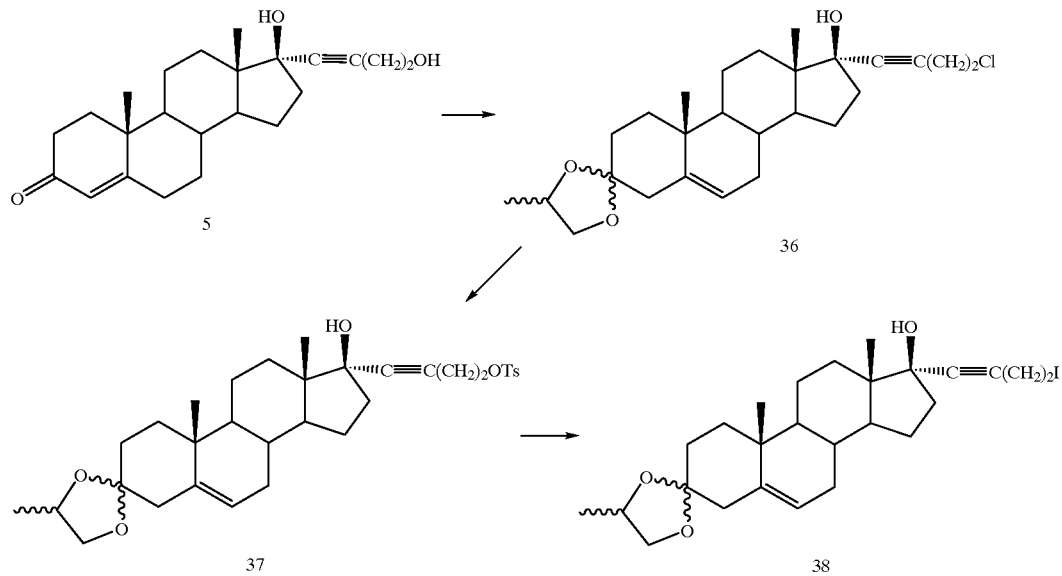

SCHEME 12

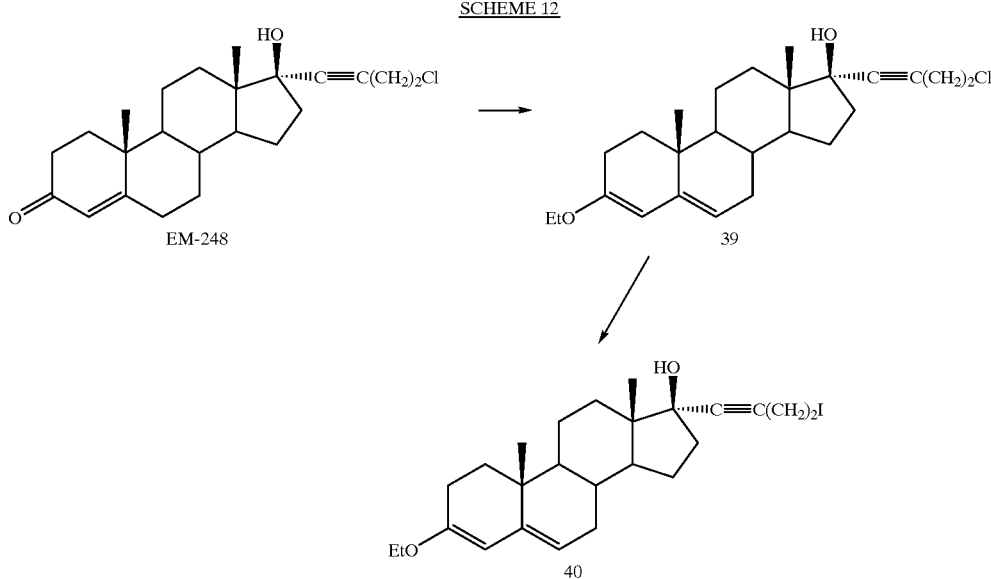

The antiandrogens of the invention which include prodrugs are preferably formulated together with pharmaceutically acceptable diluent or carrier into pharmaceutical compositions at conventional antiandrogen concentrations for antiandrogens used in the prior art. The attending clinician may elect to modify the concentration and/or dosage in order to adjust the dose to the particular response of each patient. Preferably, the attending clinician will, especially at the beginning of treatment, monitor an individual patient's overall response and serum levels of antiandrogen (in comparison to the preferred serum concentrations discussed above), and monitor the patient's overall response to treatment, adjusting dosages as necessary where a given patients' metabolism or reaction to treatment is atypical. Capsules having the antiandrogens discussed herein may also be utilized. As discussed in more detail below, carriers or diluents include solids and liquids. When a composition is prepared other than for immediate use, an art-recognized preservative is typically included (e.g. benzyl alcohol). The novel pharmaceutical compositions of the invention may be used in the treatment of androgen-related diseases. When administered systemically (e.g., for treatment of prostate cancer, benign prostatic hyperplasia, and other diseases not primarily affecting the skin) conventional diluents or carriers which are known in the art to be pharmaceutically acceptable for systemic use are used, e.g., saline, water, aqueous ethanol, oil, etc. The carrier is often a mixture of ingredients.

When formulated for systemic use, the antiandrogens may be prepared for administration in conventional ways such as orally or by injection. The antiandrogen can be administered, for example, by the oral route. The compounds of the present invention may be formulated with conventional pharmaceutical excipients, (e.g. spray dried lactose and magnesium stearate) into tablets or capsules for oral administration. Of course, taste-improving substances can be added in the case of oral administration forms. When capsules for oral ingestion are desired, any pharmaceutical capsules known in the art may be filled with the active ingredients of the invention, with or without additional diluents and other additives discussed herein.

The active substance can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol.

As further forms, one can use plug capsules, e.g. of hard gelatin, as well as closed solf-gelatin capsules comprising a softner or plasticizer, e.g. glycerine. The plug capsules contain the active substance preferably in the form of granulate, e.g. in mixture with fillers, such as lactose, saccharose, mannitol, starches, such as potato starch or amylopectin, cellulose derivatives or highly dispersed silicic acids. In solf-gelatin capsules, the active substance is preferably dissolved or suspended in suitable liquids, such as vegetable oils or liquid polyethylene glycols.

A dry delivery system, as described in U.S. Pat. Nos. 3,742,951, 3,797,494 or 4,568,343 may be used.

Alternatively, the active ingredient may be placed into a transdermal patch having structures known in the art, for example, structures such as those set forth in E.P. Patent No.0279982.

Solvents or devices as described in U.S. Pat. Nos. 5,064,654, 5,071,644 or 5,071,657 can also be used to facilitate transdermal penetration when systemic effects are desired. When used to treat systemic diseases, the site of application on the skin should be changed in order to avoid excess local concentration of steroids.

In preferred embodiments, the inhibitors of the invention are utilized for the treatment of androgen related diseases of the skin such as acne, seborrhea, hirsutism, androgenic alopecia and premature male baldness. When used for any fo these purposes, the antiandrogens are preferably administered topically together with a conventional topical carrier or diluent. When used topically, it is preferred that the diluent or carrier does not promote transdermal penetration of the active ingredients into the blood stream or other tissues where they might cause unwanted systemic effects.

When the compound is administered in a cutaneous or topical carrier or diluent, the carrier or diluent may be any chosen from many that are known in the cosmetic and medical arts, e.g. any gel, cream, lotion, ointment, liquid or non liquid carrier, emulsifier, solvent, liquid diluent or other similar vehicle which does not exert deleterious effect on the skin or other living animal tissue. The carrier or diluent is usually a mixture of several ingredients, including, but not limited to liquid alcohols, liquid glycols, liquid polyalkylene glycols, water, liquid amides, liquid esters, liquid lanolin and lanolin derivatives and similar materials. Alcohols include mono and polyhydric alcohols, including ethanol, glycerol, sorbitol, isopropanol, diethylene glycol, propylene glycol, ethylene glycol, hexylene glycol, mannitol and methoxyethanol. Typical carriers may also include ethers, e.g. diethyl and dipropyl ether, methoxypolyoxyethylenes, carbowaxes, polyethyleneglycerols, polyoxyethylenes and sorbitols. Usually, the topical carrier includes both water and alcohol in order to maximize the hydrophylic and lipophylic solubility, e.g. a mixture of ethanol or isopropanol with water.

A topical carrier may also include various other ingredients commonly used in ointments and lotions and well known in the cosmetic and medical arts. For example, fragrances, antioxidants, perfumes, gelling agents, thickening agents such as carboxymethylcellulose, surfactants, stabilizers, emollients, coloring agents and other similar agents may be present.

The concentration of active ingredient in the ointment, cream, gel or lotion is typically from about 3 to 20 percent preferably between 5 and 10 percent and most preferably 5 percent (by weight relative to the total weight of the lotion, cream, gel or ointment). Within the preferred ranges, higher concentrations allow a suitable dosage to be achieved while applying the lotion, ointment, gel or cream in a lesser amount or with less frequency.

The following non-limiting examples describe the preparation of a typical cream, lotion, gel and ointment, respectively. In addition to these vehicles, one skilled in the art may choose other vehicles in order to adapt to specific dermatologic needs.

EXAMPLE 23

Topical lotion

| Ingredient | % by Weight of Total Composition |
|---|---|
| Antiandrogen (e.g. EM-250) | 5.0 |
| Ethanol | 47.5 |
| Propylene glycol | 47.5 |

EXAMPLE 24

Topical cream

| Ingredient | % by Weight of Total Composition |
|---|---|
| Antiandrogen (e.g. EM-250) | 5 |
| Ethanol | 31 |
| Emulsitying Wax N.F. | 15.5 |
| Light mineral oil N.F. | 9.45 |
| Purified water | 34.55 |
| Methyl Paraben N.F. | 0.2 |
| citric acid | 3.7 |
| Propyl Paraben USP | 0.2 |
| Germall 115 (available from Anisol Canada) | 0.4 |

EXAMPLE 25

Topical gel

| Ingredient | % by Weight of Total Composition |
|---|---|
| Antiandrogen (e.g. EM-250) | 5.0 |
| Ethanol | 50.0 |
| Glycerin | 11.0 |
| Carbopol 940 (polyacrylic acid) | 1.0 |
| triethanolamine. | 0.2 |
| Purified water | 32 |
| Methyl Paraben USP | 0.4 |
| Propyl Paraben USP | 0.4 |

When antiandrogens are administered systemically, they are preferably administered orally or parenterally. Naturally, topical administration is preferred when the desired site of action is the skin.

Concentration of active expedient varies in a known manner depending upon the method of administering the pharmaceutical composition. A composition suitable for oral administration may preferably include at least one inhibitor of antiandrogens wherein the total concentration of all such antiandrogens in said pharmaceutical composition is from about 1% to 95% of the composition (by weight), and preferably from about 5% to about 20%. Where a combination of antiandrogens is used, the total dosage of the sum of all antiandrogens should be equal to the dosage range recited above. Blood level of the antiandrogen a preferred criteria of adequate dosage which takes into account individual variation in absorption and metabolism. The pharmaceutically acceptable diluent is preferably starch or lactose (with or without tartrazine).

When prepared for parental injection, the antiandrogen is preferably added at a concentration between about 1.0 mg/ml and about 100 mg/ml (preferably about 2.0 mg/ml to about 10 mg/ml).

When systemic activity is desired, it is necessary only that the antiandrogen be administered in a manner and at a dosage sufficient to allow blood serum concentration to obtain desired levels. Serum antiandrogen concentration should typically be maintained between 10 and 2000 micrograms per liter, preferably between 100 and 1000 micrograms per liter and most preferably between 200 and 500 micrograms per liter. Adequate serum levels may also be assessed by a patients response to therapy.

For typical patients, the appropriate dosage of the antiandrogen to achieve desired serum concentration is between 10 and 2000 milligrams of active ingredient per day per 50 kg of body weight when administered orally. When administered by injection, about 1 to 2000 mg per day per 50 kg of body weight is recommended, preferably from 10 to 100.

For topical use the lotion, ointment, gel or cream should be thoroughly rubbed into the skin so that no excess is plainly visible, and the skin is preferably not be washed in that region for at least 30 minutes. The amount applied should provide at least 0.02 milligrams of antiandrogen per square centimeter (preferably from 0.1 to 1 mg/cm2) per application. It is desirable to apply the topical composition to the effected region from 1 to 6 times daily, e.g. 3 times daily at approximately regular intervals. In some embodiments of the invention, the antiandrogen of the invention are used in combination with another active ingredient as part of a combination therapy. For example, the novel antiandrogen may be utilized together with a separate 5α-reductase inhibitor which may be incorporated into the same pharmaceutical composition as is the antiandrogen, or which may be separately administered. An active compound may possess both antiandrogenic and 5α-reductase inhibiting activity, and may be supplemented with another compound to reinforce either or both of these activities (e.g., another antiandrogen or another inhibitor of 5α-reductase). Combination therapy could also include treatment with one or more compounds which inhibit the production of testosterone or its precursors. In some preferred embodiments of the invention, the topical pharmaceutical composition further includes an inhibitor of steroid 5α reductase activity. One such inhibitor ("Proscar") is commercially available form Merck Sharp and Dohme. Other such inhibitors are EM-735 and EM-638. whose syntheses are as follows:

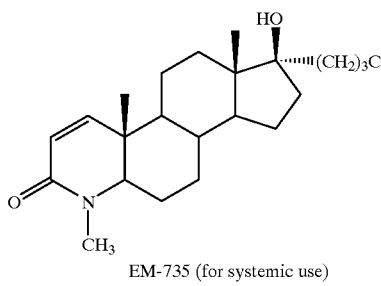

EM-735 (for systemic use)

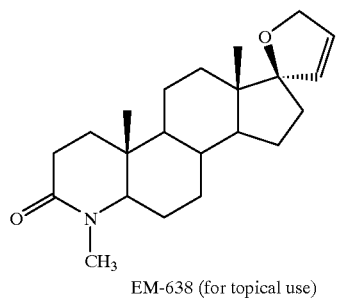

EM-638 (for topical use)

Preparation of 17β-hydroxy-17α-butyl-4-aza-5α-androst-1-en-3-one (EM-735)

17β-hydroxy-5-oxo-A-nor-3,5-secoandrostan-3-oic Acid (a)

To a stirred mixture of the testosterone acetate (available from Steraloids Inc., Wilton, N.H., USA) (200 g, 0.605 mol) in tert-butyl alcohol (2 L) was added a solution of sodium carbonate (96.3 g, 0.908 mol) in 460 mL of water. The mixture was brought to reflux and a solution of sodium periodate (893.8 g, 4.17 mol) and potassium permanganate (70.8 g, 0.45 mol) in warm water (75° C.) was added gradually (1 h) while the reflux temperature was maintained. The reaction was cooled to 30° C., and after 15 min. the solids were removed by filtration. The solid was washed with 800 mL of water, and the combined filtrates were concentrated under reduced pressure to remove most of tert-butyl alcohol (final volume 1.0 L). The aqueous residue was cooled and acidified to pH 3.0 with concentrated hydrogen chloride solution. The aqueous solution was extracted with methylene chloride (4×800 mL) and the combined organic phase was washed with water, dried and concentrated to solid. Thus the solid obtained was subjected to acetate hydrolysis by refluxing with NaOH (343 g, 0.857 mol) in methanol (2.0 L) for 12 h. The reaction mixture was concentrated to 400 mL, diluted with water (600 mL) and acidified to pH 3. The solid was filtered, washed with water and dried. The filtrate was extracted with methylene chloride (3×1.0 L), and the combined organic phases were concentrated to syrup. Both the precipitates and the syrup were swished with boiling EtOAc and cooled at 0° C. for overnight to give 125 g (67% yield) of colorless crystals; mp 205–207° C.

17β-hydroxy-4-methyl-4-aza-androst-5-ene-3-one (b)

In a Schlenk tube, MeNH$_2$ was bubbled till saturation to a mixture of the seco acid a (8.0 g, 25.98 mmol) in ethylene glycol (80 mL) at room temperature. The clear yellowish solution was heated gradually (3° C./min) up to 180° C. and held at this temperature for 1 h. The reaction mixture was cooled to 10° C. and water (80 mL) was added with stirring. The solid was filtered, washed with water (20 mL) and dried to give 6.1 g of compound b (81%); mp 181–183° C.

17β-hydroxy-4-methyl-4-aza-5α-androstan-3-one (c)

A solution of the compound b (6 g, 20.7 mmol) in acetic add (99.9%, 130 mL) was hydrogenated in the presence of platinium oxide (600 mg) at 45 p.s.i., starting at room temperature and heated to 60° C. over 12 h. The reaction mixture was cooled and filtered. The catalyst was washed with acetic add (30 mL), and the combined filtrates were concentrated to a solid (5.5 g, 91%); mp 178–180° C.

4-Methyl-4-aza-5α-androstan-3,17-dione (d)

To a stirred solution of compound c (7.3 g, 25 mmol) in methylene chloride (260 mL) was added pyridinium chlorochromate (8.1 g, 37 mmol) and the mixture was stirred at room temperature for 3 h. The contents were passed through Florisil (30–60 mesh) to remove the precipitates and the filtrates were washed with water (2×200 mL) and dried. The resulting residue was purified by "flash" column chromatography to give the dione d (4.4 g, 61%); mp 126–128° C.

17β-hydroxy-17α-(1'-butynyl)-4-methyl-4-aza-5α-androstan-3-one (EM-728)

To a solution of diisopropylamine (8.35 g, 82.51 mmol) in dry n-hexane (150 mL) at −20° C., was added n-butyllithium (33 mL, 82.5 mmol; 2.5 M in hexanes), followed by addition of 100 mL of dry diethyl ether. The mixture was stirred for 1 h at −20° C. under an argon atmosphere. 1-Butyne was bubbled (at the rate of about 1.0 g/min) into diethyl ether (10 mL) at −50° C. The cooled solution of 1-butyne in diethyl ether (5.5 eq.) was added to the LDA solution at −50° C. After 10 min, a solution of 1-butynyllithium was added to a solution of 4-methyl-4-aza-5α-androstan-3,17-dione d (5.0 g, 16.50 mmol) in diethyl ether (250 mL) at −50° C. After 1 h, the reaction was warmed to 0° C. and stirred for 12 h at room temperature. The reaction was quenched with saturated aqueous ammonia chloride (5 mL) and diluted with water (100 mL). The organic phase was separated-out and the aqueous phase was extracted with ethyl acetate (3×80 mL). The combined organic phase was dried over anhydrous magnesium sulfate, filtrated and concentrated to give the crude mixture that was purified by "flash" column chromatography ($C_6H_{14}$:$CH_3COCH_3$:EtOAc, 75:10:15 to 55:30:15) to give 4.20 g of EM-728 in 71% yield: mp 155–157° C.; IR ν cm$^{-1}$ (KBr) 3335, 2947, 2870, 1624, 1609, 1444, 1399, 1316, 1240, 1052, 1024; $^1$H-NMR δ (CDCl$_3$, 300 MHz, TMS): 0.84 (s, 3 H, 18-CH$_3$), 0.90 (s, 3 H, 19-CH$_3$), 0.78–1.01 (m, 1 H), 1.15 (t, J=7.6, 7.6 Hz, 3 H, 4'- CH$_3$), 1.25–1.49 (m, 9 H), 1.50–1.69 (m, 4 H), 1.78–1.92 (m, 2 H), 1.96 (dd, J=2.0, 2.1 Hz, 1 H), 2.00 (ddd, J=3.0, 7.4, 12.0 Hz, 2 H), 221 (ddd, J=3.0, 5.1, 10.3 Hz, 1 H), 2.24 (q, J=7.6 Hz, 2 H, 3° CH$_2$), 2.44 (dd, J=4.7, 9.5 Hz, 2 H), 2.93 (s, 3 H, 4-NCH$_3$), 3.14 (s, 1H, OH), 3.03 (dd, J=3.6, 12.6 Hz, 1H, 5α-H); $^{13}$C-NMR δ (CDCl$_3$, 300 MHz, TMS): 170.8, 87.8 (2° C.), 82.9 (17-C), 79.8 (1'-C), 65.8, 51.7, 49.9, 47.0, 39.1, 36.5, 35.0, 33.0, 32.7, 31.6, 29.8, 29.1, 25.3, 23.0, 22.6, 20.9, 14.1, 12.9, 12.5. EI-MS m/s (relative intensity) 357 (M$^+$, 94), 342 (100), 328 (48), 262 (94), 248 (27), 206 (22), 138 (25), 124 (63), 112 (61), 96 (33), 79 (24), 70 (85). HRMS Calcd for C$_{23}$H$_{35}$O$_2$N, 357.2668.; found 357.2662.

17β-hydroxy-17α-butyl-4-aza-5α-androstan-3-one (EM-700)

To a stirred solution of the EM-728 (1.0 g, 2.80 mmol) in ethyl acetate (60 mL) was added 0.10 g of palladium on actived carbone (palladium content 10%). The flask was evacuated under 22 mm of Hg and flushed with hydrogen three times. The mixture was stirred under the H$_2$ pressure filled in a balloon for 3 h at room temperature. The reaction mixture was filtrated through Celite® 521 and with washed with ethyl acetate. Removal of the solvent gave the crude product which was passed a short "flash" silica gel column with elutent (C$_6$H$_{14}$:CH$_3$COCH$_3$, 7:3) to give 0.96 g of compound EM-700 in 95% yield: mp 147–149° C.; IR ν cm$^{-1}$ (KBr) 3417, 2948, 2866, 1628, 1457, 1429, 1395, 1305, 1237, 1112, 1026; $^1$H-NMR δ (CDCl$_3$, 300 MHz, TMS): 0.88 (s, 3 H, 18-CH$_3$), 0.90 (s, 3 H, 19-CH$_3$), 0.93 (t, J=7.1, 7.0 Hz, 3 H, 4'-CH$_3$), 0.79 (ddd, J=2.9, 4.3, 8.4 Hz, 1 H), 1.14–1.26 (m, 1 H), 1.27–1.61 (m, 18 H), 1.78–1.87 (m, 2 H), 1.98–2.04 (m, 2 H), 2.44 (dd, J=4.7, 9.5 Hz, 2 H), 2.93 (s, 3 H, 4-NCH$_3$), 2.96 (dd, J=3.5, 12.6 Hz, 1H, 5α-H); $^{13}$C-NMR S (CDCl$_3$, 300 MHz, TMS): 170.8, 83.2, 65.8, 52.0, 50.1, 46.6, 36.5 (2C), 35.3, 34.4, 33.0, 31.5, 30.0, 29.1 (2C), 25.8, 25.4, 23.6 (2C), 20.8, 14.5, 14.2, 12.4; EI-MS m/s (relative intensity) 361 (M$^+$, 86), 346 (18), 332 (47), 304 (66), 286 (49), 262 (85), 248 (56), 234 (57), 140 (40), 124 (65), 113 (84), 95 (31), 70 (100). HRMS Calcd for C$_{23}$H$_{39}$O$_2$N, 361.2980; found 361.2979.

17β-hydroxy-17α-butyl-4-aza-5α-androst-1-en-3one (EM-735)

In a 50 mL three neck round bottom flask equipped with argon inlet, reflux condenser, addition funnel, mechanical stirrer and immersion thermometer was charged with 25 mL dioxane followed by 0.96 g (2.66 mmol) of EM-700 portionwise with stirring. To this suspension was added portionwise 0.73 g (3.19 mmol) of 2,3-dichloro-5,6-dicyano-1,4-benzoquinone (DDQ). The flask was evacuated (22" Hg) and flushed with argon three times. To this stirred suspension was added bis(trimethylsilyl)trifluoroacetamide (BSTFA, 1.98 g, 7.72 mmol) via the addition funnel at rate 5 mL/min. The temperature slowly went up from 22° C. to 25° C. in a period of thirty minutes as most of the solids dissolved within this period to afford a clear solution. The solution was stirred for 18 hours at 22° C. (after which time formation of the two diastereomeric adducts were observed by TLC). The solution was then heated in an oil bath so that very gentle reflux was maintained (bath temperature 120° C., internal temperature 108° C.). After 16 hours the reaction mixture was cooled to 22° C. and poured into a mixture of 50 mL methylene chloride and 9.2 mL of 1% aqueous sodium bisulfite solution. The heterogeneous mixture was stirred for 15 min and filtered to remove the precipitate hydroquinone.

The dark red organic layer was separated and washed with 20 mL of 6 N hydrogen chloride solution followed by saturated sodium chloride solution, dried and concentrated. The crude mixture was dissolved in a mixture of tetrahydrofuran (25 mL), water (12.5 mL) and acetic acid (glacial, 25 mL) and stirred at 55° C. for 3 h. The solvents was removed to give the residue which was diluted with 40 mL of water, and extracted with dichloromethane (3×50 mL). The combined organic phases was washed with 50 mL of saturated sodium chloride solution, dried and concentrated The resulted residue was further purified by silica gel chromatography (C$_6$H$_{14}$:CH$_3$COCH$_3$, 95:5 to 70:30) to give 0.412 g (yield 43%) of desired product EM-735: mp 194–196° C.; IR ν cm$^{-1}$ (KBr) 3397, 2946, 2866, 1658, 1602, 1434, 1400, 1099, 1013, 820; $^1$H-NMR δ (CDCl$_3$, 300 MHz, TMS): 0.89 (s, 3 H, 18-CH$_3$), 0.93 (s, 3 H, 19-CH$_3$), 0.94 (t, J=7.6, 7.9 Hz, 3 H, 4'-CH$_3$), 0.90–1.01 (m, 1 H), 1.25 (dd, J=2.8, 2.4 Hz, 1 H), 1.39 (dd, J=6.7, 11.7 Hz, 1 H), 135–1.53 (m, 9 H), 1.55–1.60 (m, 4 H), 1.61–1.66 (m, 2 H), 1.78 (dd, J=3.3, 11.7 Hz, 1 H), 1.85 (dd, J=3.4, 13.2 Hz, 1 H), 1.97 (t, J=3.0, 3.3 Hz, 1 H), 1.97 (dd, J=4.2, 8.5 Hz, 1 H), 2.95 (s, 3 H, 4-NCH$_3$), 3.32 (dd, J=3.7, 13.1 Hz, 1 H, 5αH), 5.84 (d, J=9.6 Hz, 1 H, 2-H), 6.69 (d, J=9.9 Hz, 1 H, 1-H); $^{13}$C-NMR δ (CDCl$_3$, 300 MHz, TMS): 165.6, 148.7, 123.2, 83.2, 63.9, 50.0, 47.9, 46.7, 39.6, 36.5, 35.6, 34.4, 31.5, 29.8, 27.6, 24.4, 23.6 (2 C), 21.0, 14.6, 14.2, 12.2; EI-MS m/s (relative intensity) 359 (M$^+$, 86), 344 (12), 302 (32), 284 (15), 260 (81), 246 (27), 232 (26), 137 (44), 124 (100), 113 (46), 70 (53). HRMS Calcd for C$_{23}$H$_{37}$O$_2$N, 359.2824; found 359.2805.

Preparation of 17(2',3'α)-2',5'-dihydrofuran-4-methyl-4aza-5α-androstan-3-one (EM-638)

17β-hydroxy-17α-(3'-hydroxy-1'-propenyl)-4-methyl-4-aza-5α-androstan-3-one

To the alkyne (100 mg, 0288 mmol) in 10 ml of anhydrous pyridine was added 30 mg of Pd/CaCO$_3$. The solution was purged three times with hydrogen alternating with vaccum, and then hydroganated over a period of 3 h at room temperature and atmospheric pressure. When no more starting material left, the reaction mixture was filtered over Celite to give the crude product which was "flash" chromatographed using CH$_2$Cl$_2$:CH$_3$OH (9:1) as eluant to provide 73 mg of the product (73%).

17(2',3'α)-2',5'-dihydrofuran-4-methyl-4-aza-a-androstan-3-one (EM-638)

A solution of 17β-hydroxy-17α-(3'-hydroxy-1'-propenyl)-4-methyl-4-aza-5α-androstan-3-one (730 mg, 2.0 mmol) in 30 mL of anhydrous pyridine was added p-TsCl (800 g, 4.0 mmol) and stirred for 6 h at room temperature. Pyridine was evaporated and the reaction mixture was extracted with CH$_2$Cl$_2$. The crude mixture was purified by a "flash" chromatography using CH$_2$Cl$_2$: CH$_3$OH (9:1) as eluant, to give 420 mg of EM-638 in 88% yield. IR ν cm$^{-1}$ (KBr) 3045 (double bond), 1646 (amide); $^1$H-NMR δ (CDCl$_3$, 300 MHz, TMS): 0.87 (s, 3 H, 18-CH$_3$), 0.88 (s, 3 H, 19-CH$_3$), 2.41 (dd, J=4.5, 9.3 Hz, 2 H), 2.90 (s, 3 H, 4-NCH$_3$), 3.0 (dd, J=3.5, 12.5 Hz, 1 H, 5α-H), 4.52 (m, 2 H, O—CH$_2$), 5.78 (m, 2 H, CH=CH). $^{13}$C NMR (CDCl$_3$) d 170.8, 132.1, 124.4, 100.6, 74.4, 65.8, 52.0, 50.8, 45.8, 36.4, 35.5, 34.8, 32.9, 32.9 (2 C), 29.8, 29.1, 29.0, 25.3, 23.1, 20.6, 14.2, 12.3. HRMS Calcd for C$_{22}$H$_{33}$O$_2$N, 343.2502; found 343.2524.

The 5α-reductase inhibitor is formulated at conventional concentrations and administered at conventional dosages, e.g., at the same concentrations and dosages set forth above for the anti-androgen.

A combination therapy involving 5α-reductase inhibitor and antiandrogen has the beneficial effect of inhibiting activation of androgen receptors by two different mechanisms without significantly reducing testosterone levels, the reduction of which may cause undesirable side effects in some patients. In appropriate cases, i.e. where prostate cancer or another androgen related disease is not responding acceptably to treatment, a concurrent therapy designed to decrease testosterone levels may also be utilized (e.g., surgical or chemical castration, for example, by administering a LHRH agonists or antagonists known in the art).

Although the present invention has been described in relation to particular embodiments thereof, many other variations and modifications and other uses will become apparent to those skilled in the art. The present invention as defined by the claims is thus not to be limited to the specific disclosure herein.

What is claimed is:

1. A method of treating or reducing the risk of acquiring a condition selected from the group consisting of acne, seborrhea, comprising administering to a patient in need of such treatment or reduction a therapeutically effective amount of an antiandrogenic compound of the molecular formula:

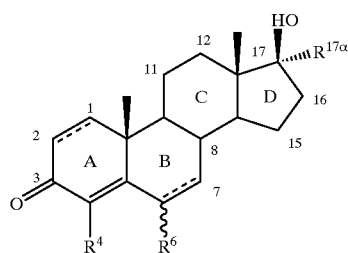

wherein the dotted lines are optional π bonds;
wherein $R^4$ is —H or —CH$_3$;
wherein $R^6$ is —H, —CH$_3$, —CH$_2$CH$_3$ or halogen, but is hydrogen when the optional π bond at 6,7 is present;
and wherein $R_{17\alpha}$ is selected from the group consisting of:
A) a halogenated unsaturated hydrocarbon moiety having at least one halogen atom that is separated from said D-ring by at least 3 intervening atoms, and having no carbon atom separated from said D-ring by more than four intervening atoms; and
B) a haloalkyl moiety having at least one halogen atom separated from said D-ring by at least three intervening atoms and having no carbon atom separated from said D-ring by more than 4 intervening atoms; provided that $R^{17\alpha}$ is not

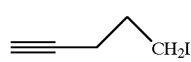

CH$_2$X when $R^4$ or $R^6$ are both hydrogen (x being halogen).

2. The method of claim 1, wherein said antiandrogenic compound has a molecular formula:

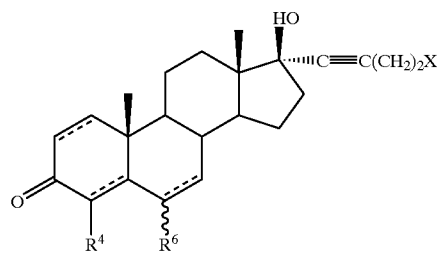

wherein X is chlorine, bromine or iodine.

3. The method of claim 2, wherein said condition is acne.

4. The method of claim 2, wherein said condition is seborrhea.

5. A method of treating or reducing the risk of acquiring a condition selected from the group consisting of acne, seborrhea, comprising administering to a patient in need of such treatment or reduction a therapeutically effective amount of an antiandrogenic compound of the molecular formula:

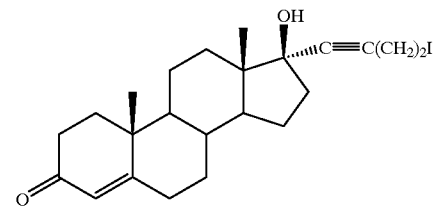

6. A method of treating or reducing the risk of acquiring a condition selected from the group consisting of acne, seborrhea, comprising administering to a patient in need of such treatment or reduction a therapeutically effective amount of an antiandrogenic compound selected from the group consisting of:

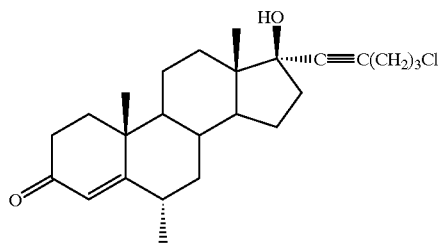

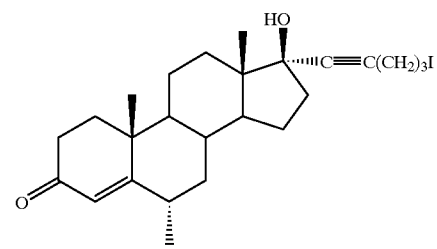

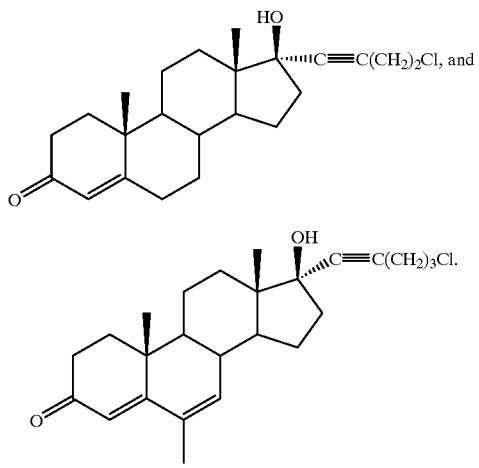
7. The method of claim 6 wherein said antiandrogenic compound is:
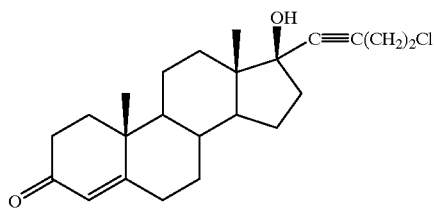
* * * * *